(12) United States Patent
Richards

(10) Patent No.: US 11,529,369 B2
(45) Date of Patent: Dec. 20, 2022

(54) METHODS AND COMPOSITIONS FOR GENETIC MODULATION

(71) Applicant: RDG Holdings, Inc., Pleasant Grove, UT (US)

(72) Inventor: Kurt Richards, Herriman, UT (US)

(73) Assignee: RDG HOLDINGS, INC., Pleasant Grove, UT (US)

( * ) Notice: Subject to any disclaimer, the term of this patent is extended or adjusted under 35 U.S.C. 154(b) by 725 days.

(21) Appl. No.: 16/212,096

(22) Filed: Dec. 6, 2018

(65) Prior Publication Data
US 2019/0192558 A1 Jun. 27, 2019

Related U.S. Application Data

(60) Provisional application No. 62/609,984, filed on Dec. 22, 2017.

(51) Int. Cl.
| | |
|---|---|
| A61K 33/20 | (2006.01) |
| A61K 33/40 | (2006.01) |
| A61K 9/00 | (2006.01) |
| C25B 1/13 | (2006.01) |
| C25B 1/26 | (2006.01) |
| C25B 1/02 | (2006.01) |
| C25B 1/30 | (2006.01) |

(52) U.S. Cl.
CPC ............ *A61K 33/20* (2013.01); *A61K 9/0053* (2013.01); *A61K 33/40* (2013.01); *C25B 1/02* (2013.01); *C25B 1/13* (2013.01); *C25B 1/26* (2013.01); *C25B 1/30* (2013.01)

(58) Field of Classification Search
None
See application file for complete search history.

(56) References Cited

U.S. PATENT DOCUMENTS

2012/0039958 A1 * 2/2012 Watson ................ A61K 31/137
424/400

OTHER PUBLICATIONS

Pan et al., "Cutting Edge: A Novel Chemokine Ligand for CCR10 And CCR3 Expressed by Epithelial Cells in Mucosal Tissues" 165 The Journal of Immunology 2943-2949 (Year: 2000).*

* cited by examiner

*Primary Examiner* — Nancy J Leith
(74) *Attorney, Agent, or Firm* — Knobbe, Martens, Olson & Bear LLP

(57) ABSTRACT

Described herein are methods for modulating expression of a gene in a cell by contacting the cell with a gene modulation composition, such as a composition including an electrolyzed saline solution.

24 Claims, 14 Drawing Sheets
(9 of 14 Drawing Sheet(s) Filed in Color)

METHODS AND COMPOSITIONS FOR GENETIC MODULATION

RELATED APPLICATIONS

This application claims the benefit of priority to U.S. Provisional Patent Application No. 62/609,984, filed Dec. 22, 2017, the disclosure of which is incorporated by reference herein in its entirety.

FIELD

The present disclosure relates to methods and compositions for modulating gene expression in a cell. More particularly, the present disclosure relates to a composition including an electrolyzed saline solution having a mixture of reduced species and reactive species formulated for gene modulation in a subject.

BACKGROUND

Gene expression, the process of conversion of genetic information into a function genetic product is a tightly regulated process in living organisms. Gene expression takes place by transcription of the nucleotide sequence of a gene into a nucleotide sequence of a functional RNA or translation into an amino acid sequence of a protein. Regulation of gene expression includes regulation of mRNA stability and translation, and is important in cellular responses to development or to environmental stimuli such as nutrient levels, cytokines, hormones, and temperature shifts, and environmental stresses such as hypoxia, hypocalcemia, viral infection, and tissue injury. The genes respond according to these stimuli, resulting in a downstream response.

SUMMARY

The present disclosure is directed to compositions and methods for modulating expression of a gene in a cell.

Some embodiments provided herein relate to a method of modulating expression of a gene in a cell. In some embodiments, the method includes contacting the cell with a composition including an electrolyzed saline solution. In some embodiments, the electrolyzed saline solution includes a mixture of reduced species and reactive oxygen species. In some embodiments, contacting the cell with the electrolyzed saline solution modulates expression of a gene. In some embodiments, modulating expression of the gene includes changing expression of the gene. In some embodiments, the method further includes detecting the change in expression of the gene.

In some embodiments, a gene that has modulated expression includes a gene encoding C-C chemokine receptor type 10 (CCR10), coiled-coil domain-containing protein 126 (CCDC126), DnaJ homolog subfamily C member 3 (DNAJC3), early growth response protein 1 (EGR1), embigin (EMB), immunoglobulin lambda variable 1-41 (IGLV1-41), immunoglobulin lambda variable 1-51 (IGLV1-51), interleukin-1 receptor-associated kinase 3 (IRAK3), potassium channel tetramerization domain containing 12 (KCTD12), pyridine nucleotide-disulfide oxidoreductase domain 1 (PYROXD1), or WD repeat-containing protein 11 (WDR11).

In some embodiments, expression of the gene is modulated by greater than 2 fold change compared to expression of the gene in an untreated cell. In some embodiments, gene expression is increased in CCDC126, CCR10, EGR1, IGLV1-41, or IGLV1-51. In some embodiments, gene expression is decreased in DNAJC3, EMB, IRAK3, KCTD12, PYROXD1, or WDR11.

In some embodiments, the cell is an isolated cell. In some embodiments, the cell is located in situ in a subject. In some embodiments where the cell is located in situ in a subject, a change in expression of the gene is detected by inferring a change in the expression of the gene from a physiological change in the subject. In some embodiments, detecting includes performing one or more of ELISA, immunohistochemistry, Northern blot, Southern blot, or PCR.

In some embodiments, when the cell is located in situ in a subject, contacting includes administering to the subject an amount of the composition effective to modulate expression of the gene. In some embodiments, the subject is human. In some embodiments, the composition is administered orally. In some embodiments, the composition is administered in an amount of about 0.1 ounce to about 12 ounces at a frequency of four times daily to one time monthly for a period of one day to 10 years.

In some embodiments, the composition has a pH between about 6 and about 9. In some embodiments, the composition includes a solution containing 1000 ppm to 1400 ppm sodium, 1200 ppm to 1600 ppm chloride, 16 ppm to 24 ppm hypochlorous acid, at least 94 µM superoxide radical, and at least 241 µM hydroxyl radical. In some embodiments, the electrolyzed saline solution includes $HOCl^{-1}$, $OCl^{-1}$, $Cl^{-1}$, $Cl_2$, $O_2^{3}$, $O_3$, and $H_2O_2$. In some embodiments, the one or more active species includes one or more of active chlorine species in an amount of about 5 to about 300 ppm, active oxygen species in an amount of about 0.1 to about 300 ppm, or active hydrogen species in an amount of about 5 to about 300 ppm, or combinations thereof. In some embodiments, the active chlorine species includes at least one of an active chlorine species including free chlorine, hypochlorous acid, and/or hypochlorite ion, or combinations thereof.

In some embodiments, the electrolyzed saline solution is prepared by subjecting a saline solution including sodium chloride in an amount of about 0.05 to about 10% to electrolysis under conditions sufficient to produce the one or more active species. In some embodiments, the electrolyzed saline solution is prepared using a saline solution with a starting sodium chloride solution of 0.1% to 5% NaCl (wt/vol), such as 0.9% NaCl (w/vol), 0.45% NaCl (w/vol), or 0.215% NaCl (wt/vol).

BRIEF DESCRIPTION OF THE DRAWINGS

In addition to the features described above, additional features and variations will be readily apparent from the following descriptions of the drawings and exemplary embodiments. It is to be understood that these drawings depict typical embodiments, and are not intended to be limiting in scope. The patent or patent application file contains at least one drawing executed in color. Copies of this patent or patent application publication with color drawings will be provided by the Office upon request and payment of the necessary fee.

FIG. 2A includes samples 1-30 and FIG. 2B includes samples 31-60.

DETAILED DESCRIPTION

Figure 1:
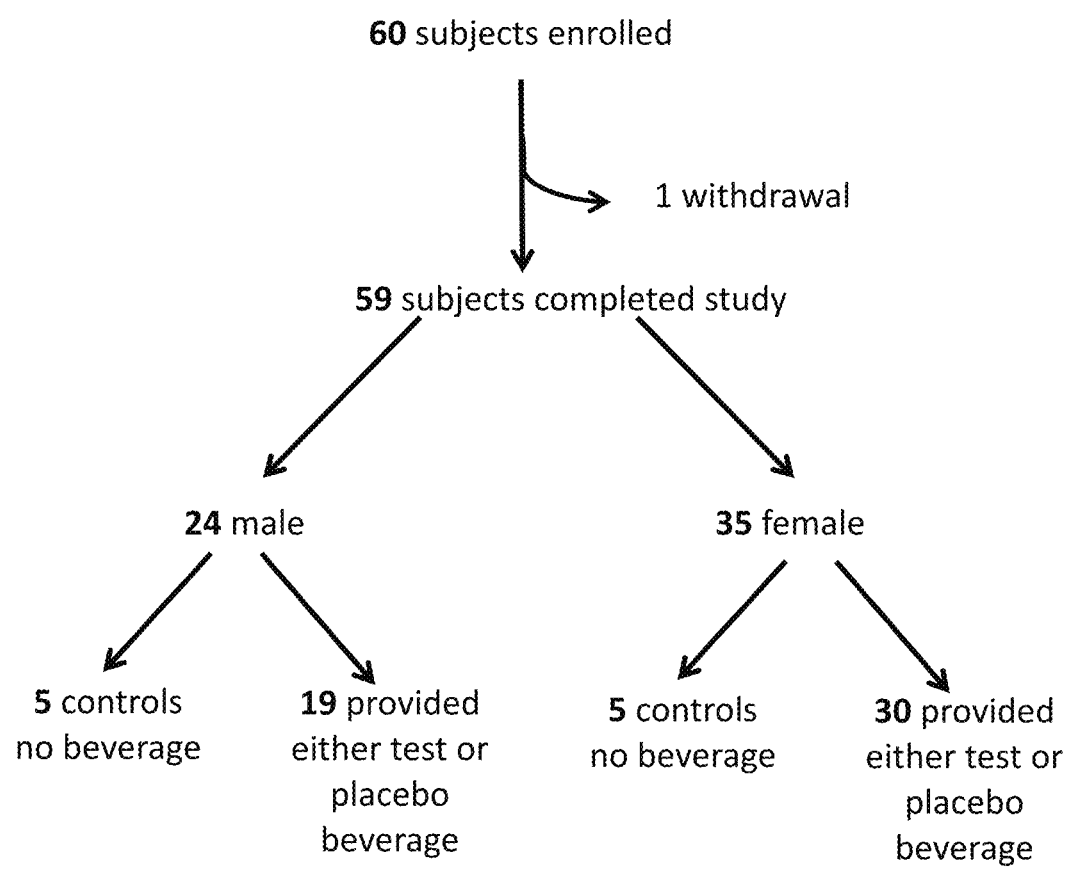
FIG. 1 depicts a schematic representation of certain embodiments of subject selection and experimental treatment design.

Embodiments provided herein related to compositions and methods for modulating gene expression. In certain embodiments, a composition includes an electrolyzed saline solution including a mixture of reduced species and reactive species. In certain embodiments, the composition is formulated for administration to a subject, and upon administration, gene expression in the subject is modulated.

It will be readily understood that the aspects of the present disclosure, as generally described herein, can be arranged, substituted, combined, separated, and designed in a wide variety of different configurations, all of which are explicitly contemplated herein.

Unless defined otherwise, technical and scientific terms used herein have the same meaning as commonly understood by one of ordinary skill in the art to which the present disclosure belongs. All patents, applications, published applications and other publications referenced herein are expressly incorporated by reference in their entireties unless stated otherwise. For purposes of the present disclosure, the following terms are defined below.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. When a value is preceded by the term about, the component is not intended to be limited strictly to that value, but it is intended to include amounts that vary from the value.

Throughout this specification, unless the context requires otherwise, the words "comprise," "comprises," and "comprising" will be understood to imply the inclusion of a stated step or element or group of steps or elements but not the exclusion of any other step or element or group of steps or elements.

As used herein, a "subject" or a "patient" refers to an animal that is the object of treatment, observation, or experiment. "Animal" comprises cold- and warm-blooded vertebrates and invertebrates such as fish, shellfish, reptiles and, in particular, mammals. "Mammal" comprises, without limitation, mice, rats, rabbits, guinea pigs, dogs, cats, sheep, goats, cows, horses, primates, such as monkeys, chimpanzees, and apes, and, in particular, humans. In some alternatives, the subject is human.

Gene Modulating Compositions and Methods of Making Same

Described herein are compositions for modulating expressing of a gene in a cell upon contact of the composition with a cell. The composition can include fluids that can be administered to a subject. The composition includes an electrolyzed saline solution that generally includes at least one redox signaling agent (RSA). RSAs can include, but are not limited to superoxides: $O_2^{*-}$, $HO_2^*$; hypochlorites: $OCl^-$, $HOCl$, $NaOCl$; hypochlorates: $HClO_2$, $ClO_2$, $HClO_3$, $HClO_4$; oxygen derivatives: $O_2$, $O_3$, $O_4^{*-}$, $^1O$; hydrogen derivatives: $H_2$, $H^-$; hydrogen peroxide: $H_2O_2$; hydroxyl free radical: $OH^{*-}$; ionic compounds: $Na^+$, $Cl^-$, $H^+$, $OH^-$, $NaCl$, $HCl$, $NaOH$; chlorine: $Cl_2$; water clusters: $n*H_2O$-induced dipolar layers around ions, and combinations thereof. Some RSAs are electron acceptors and include $HOCl$, $NaClO$, $O_2$, $H_2$, $H^+$, $ClO$, $Cl_2$, $H_2O_2$ and some are electron donors and include $O_2^-$, $HO_2$, $Cl^-$, $H^-$, $*OCl$, $O_3$, $*O_2^-$ and $OH^-$.

The terms "composition" or "formulation" as used herein refer to their generally accepted meaning in the art. These terms generally refer to a composition or formulation, such as in a pharmaceutically acceptable carrier or diluent, in a form suitable for administration, for example, systemic or local administration, into a cell or subject, including, for example, a human. Suitable forms, in part, depend upon the use or the route of entry, for example in vitro contact to a cell in isolation or administration to a cell located in situ in a subject by administration via oral, transdermal, inhalation, or by injection. Such forms should not prevent the composition or formulation from reaching a target cell. For example, compositions injected into the blood stream should be soluble. Other factors are known in the art, and include considerations such as toxicity and forms that prevent the composition or formulation from exerting its effect. As used herein, pharmaceutical formulations include formulations for human and veterinary use. A "pharmaceutically acceptable composition" or "pharmaceutically acceptable formulation" can refer to a composition or formulation that allows for the effective distribution of the electrolyzed saline solution to the physical location most suitable for gene modulation.

Methods of making the gene modulating compositions are described including electrolyzed saline solution having a salt concentration of about 10 g NaCl/gal, such as 10.75 g NaCl/gal using a set of electrodes with an amperage of about 50-60 amps, such as 56 amps to produce an electrolyzed saline solution, wherein the water is chilled below room temperature and the water is circulated during electrolyzing.

A method of producing the disclosed compositions can include one or more of the steps of (1) preparation of an ultra-pure homogeneous solution of sodium chloride in water, (2) temperature control and flow regulation through a set of inert catalytic electrodes and (3) a modulated electrolytic process that results in the formation of such stable molecular moieties and complexes. In one embodiment, such a process includes all these steps.

The saline generally should be free from contaminants, both organic and inorganic, and homogeneous down to the molecular level. In particular, metal ions can interfere with the electro-catalytic surface reactions, and thus it may be helpful for metals to be avoided. In one embodiment, a brine solution is used to salinate the water. The brine solution can have a NaCl concentration of about 540 g NaCl/gal, such as 537.5 g NaCl/gal. In one embodiment, the composition can include at least one species such as $O_2$, $H_2$, $Cl_2$, $OCl^-$, HOCl, NaOCl, $HClO_2$, $ClO_2$, $HClO_3$, $HClO_4$, $H_2O_2$, $Na^+$, $Cl^-$, $H^+$, $H^-$, $OH^-$, $O_3$, $O_4^{*-}$, $^1O$, $OH^{*-}$, $HOCl-O_2^{*-}$, $HOCl-O_3$, $O_2^{*-}$, $HO_2^*$, NaCl, HCl, NaOH, water clusters, or a combination thereof.

In one embodiment, the composition can include at least one species such as $H_2$, $Cl_2$, $OCl^-$, HOCl, NaOCl, $HClO_2$, $ClO_2$, $HClO_3$, $HClO_4$, $H_2O_2$, $O_3$, $O_4^{*-}$, $^1O_2$, $OH^{*-}$, $HOCl-O_2^{*-}$, $HOCl-O_3$, $O_2^{*-}$, $HO_2^*$, water clusters, or a combination thereof.

In one embodiment, the composition can include at least one species such as $HClO_3$, $HClO_4$, $H_2O_2$, $O_3$, $O_4^{*-}$, $^1O_2$, $OH^{*-}$, $HOCl-O_2^{*-}$, $HOCl-O_3$, $O_2^{*-}$, $HO_2^*$, water clusters, or a combination thereof.

In one embodiment, the composition can include at least $O_2^*-$ and HOCl.

In one embodiment, the composition can include $O_2$. In one embodiment, the composition can include $H_2$. In one embodiment, the composition can include $Cl_2$. In one embodiment, the composition can include $OCl^-$. In one embodiment, the composition can include HOCl. In one embodiment, the composition can include NaOCl. In one embodiment, the composition can include $HClO_2$. In one embodiment, the composition can include $ClO_2$. In one embodiment, the composition can include $HClO_3$. In one embodiment, the composition can include $HClO_4$. In one embodiment, the composition can include $H_2O_2$. In one embodiment, the composition can include $Na^+$. In one embodiment, the composition can include $Cl^-$. In one embodiment, the composition can include $H^+$. In one embodiment, the composition can include $H^-$. In one embodiment, the composition can include $OH^-$. In one embodiment, the composition can include $O_3$. In one embodiment, the composition can include $O_4^{*-}$. In one embodiment, the composition can include $^1O_2$. In one embodiment, the composition can include $OH^{*-}$. In one embodiment, the composition can include $HOCl-O_2^{*-}$. In one embodiment, the composition can include $HOCl-O_3$. In one embodiment, the composition can include $O_2^{*-}$. In one embodiment, the composition can include $HO_2^*$. In one embodiment, the composition can include NaCl. In one embodiment, the composition can include HCl. In one embodiment, the composition can include NaOH. In one embodiment, the composition can include water clusters. Embodiments can include combinations thereof.

In one embodiment, the method of making a formulation as described herein can include reverse osmosis. As used herein, the term "reverse osmosis" refers to a process of extracting water through a semi-permeable membrane from feed water by applying on the feed water a pressure that is higher than the osmotic pressure of the feed water. Water can be supplied from a variety of sources, including but not limited to municipal water, filtered water, distilled water, nanopure water, or the like.

The reverse osmosis process can vary, but can include providing water having a total dissolved solid content of less than about 10 ppm, such as about 9 ppm, about 8 ppm, about 7 ppm, about 6 ppm, about 5 ppm, about 4 ppm, about 3 ppm, about 2 ppm, about 1 ppm or less.

The reverse osmosis process can be performed at a temperature of about 5° C., about 10° C., about 15° C., about 20° C., about 25° C., about 30° C., about 35° C., or a temperature within a range defined by any two of the aforementioned values. The reverse osmosis step can be repeated as needed to achieve a particular total dissolved solids level. In some embodiments, a distillation step can also be performed, prior to, after, or concomitant with the reverse osmosis step. Distillation as used herein refers to a process boiling water and condensing steam into a separate container to obtain distilled water. Distilled water includes water that is purified to remove minerals such as calcium and magnesium, trace elements, or other impurities by distillation.

Other means of reducing contaminants include filtration and/or purification such as by utilizing deionization, carbon filtration, double-distillation, electrodeionization, resin filtration such as with Milli-Q purification, microfiltration, ultrafiltration, ultraviolet oxidation, electrodialysis, or combinations thereof.

The distillation process can vary, but can provide water having a total dissolved solid content of less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or less, or an amount within a range defined by any two of the aforementioned values. The temperature of the distillation process can be performed at a temperature of about 5° C., about 10° C., about 15° C., about 20° C., about 25° C., about 30° C., about 35° C., or a temperature within a range defined by any two of the aforementioned values.

The distillation step can be repeated as needed to achieve a particular total dissolved solids level. After water has been subjected to reverse osmosis, distillation, both, or neither, the level of total dissolved solids in the water can be less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or less, or an amount within a range defined by any two of the aforementioned values.

The reverse osmosis, distillation, both, or neither, can be preceded by a carbon filtration step.

Purified water can be used directly with the systems and methods described herein.

In one embodiment, contaminants can be removed from a commercial source of water by the following procedure: water flows through an activated carbon filter to remove the aromatic and volatile contaminants and then undergoes reverse osmosis (RO) filtration to remove dissolved solids and most organic and inorganic contaminants. The resulting filtered RO water can contain less than about 8 ppm of dissolved solids. Most of the remaining contaminants can be removed through a distillation process, resulting in dissolved solid measurements less than 1 ppm. In addition to removing contaminants, distillation may also serve to condition the water with the correct structure and oxidation reduction potential (ORP) to facilitate the oxidative and reductive reaction potentials on the platinum electrodes in the subsequent electro-catalytic process.

After water has been subjected to reverse osmosis, distillation, both or neither, a salt can be added to the water in a salting step. The salt can be unrefined, refined, caked, de-caked, or the like. In some embodiments, the salt is halite, table salt, common salt, curing salt, flake salt, Epsom salt, sea salt, Alaea salt (or Hawaiian sea salt), Alpenbergkern salt, Anglesey Sea salt, Celtic sea salt, Dead Sea salt, Himalayan sea salt (including Himalayan pink sea salt), Kalahari salt, Maras salt, Murray River salt flakes, Namibian salt pearls, Persian blue fine salt, Polish mine salt, primordial sea salts, Sal de Tavira, Sale Marino di Trapani, Sel de Guérande, South African Sea salt, Utah salt, black lava salt, brine, rock salt, red rock salt, fleur de sel, or kosher salt. The salt present in the saline solution can include a number of elements, including actinium, aluminum, antimony, arsenic, astatine, barium, beryllium, bismuth, boron, bromine, cadmium, calcium, carbon, cerium, cesium, chlorine, chromium, cobalt, copper, dysprosium, erbium, europium, francium, fluorine, gadolinium, gallium, germanium, gold, hafnium, holmium, hydrogen, iodine, indium, iridium, iron, lanthanum, lead, lithium, lutetium, magnesium, manganese, mercury, molybdenum, neptunium, neodymium, nickel, niobium, nitrogen, osmium, oxygen, palladium, phosphorus, platinum, plutonium, polonium, potassium, praseodymium, promethium, protactinium, radium, rhenium, rhodium, rubidium, ruthenium, samarium, scandium, selenium, silicon, silver, sodium, strontium, sulfur, tantalum, technetium, tellurium, terbium, thallium, thorium, thulium, tin, titanium, uranium, vanadium, ytterbium, zinc, or zirconium. In some embodiments, the element present in the salt can be present in an amount of less than 0.001 ppm to an amount of greater than 400,000 ppm.

In one embodiment, the salt is sodium chloride (NaCl). In some embodiments, the salt can include an additive. Salt additives can include, but are not limited to potassium iodide, sodium iodide, sodium iodate, dextrose, sodium fluoride, sodium ferrocyanide, tricalcium phosphate, calcium carbonate, magnesium carbonate, fatty acids, magnesium oxide, silicon dioxide, calcium silicate, sodium aluminosilicate, calcium aluminosilicate, ferrous fumarate, iron, or folic acid. Any of these additives can be added at this point or at any point during the described process. For example, the above additives can be added just prior to bottling.

In another embodiment, the process can be applied to any ionic, soluble salt mixture, especially with those containing chlorides. In addition to NaCl, other non-limiting examples include LiCl, HCl, $CuCl_2$, $CuSO_4$, KCl, MgCl, $CaCl_2$, sulfates and phosphates. For example, strong acids such as sulfuric acid ($H_2SO_4$), and strong bases such as potassium hydroxide (KOH), and sodium hydroxide (NaOH) are frequently used as electrolytes due to their strong conducting abilities. Preferably the salt is sodium chloride (NaCl). A brine solution can be used to introduce the salt into the water. The amount of brine or salt needs will be apparent to one of ordinary skill in the art.

Salt can be added to water in the form of a brine solution. To mix the brine solution, a physical mixing apparatus can be used or a circulation or recirculation can be used. In one embodiment, pure pharmaceutical grade sodium chloride is dissolved in the prepared distilled water to form a 15 wt % sub-saturated brine solution and continuously re-circulated and filtered until the salt has completely dissolved and all particles >0.1 microns are removed. This step can take several days. In one embodiment, the filtered, dissolved brine solution can be injected into tanks of distilled water in about a 1:352 ratio (salt:water) in order to form a 0.3% saline solution. In one embodiment, a ratio 10.75 g of salt per 1 gallon of water can be used to form the composition. In another embodiment, 10.75 g of salt in about 3-4 g of water, such as 3,787.5 g of water can be used to form the composition. This solution then can be allowed to re-circulate and diffuse until homogeneity at the molecular scale has been achieved.

In one embodiment, the homogenous saline solution is chilled to about 4.8±0.5° C. Temperature regulation during the entire electro-catalytic process is typically required as thermal energy generated from the electrolysis process itself may cause heating. In one embodiment, process temperatures at the electrodes can be constantly cooled and maintained at about 4.8° C. throughout electrolysis.

Brine can then be added to the previously treated water or to fresh untreated water to achieve a NaCl concentration of between about 1 g NaCl/gal water and about 25 g NaCl/gal water, between about 8 g NaCl/gal water and about 12 g NaCl/gal water, or between about 4 g NaCl/gal water and about 16 g NaCl/gal water. Once brine is added to water at an appropriate amount, the solution can be thoroughly mixed. The temperature of the liquid during mixing can be at room temperature or controlled to a desired temperature or temperature range.

To mix the solution, a physical mixing apparatus can be used or a circulation or recirculation can be used. The salt solution can be chilled in a chilling step.

For large amounts of composition, various chilling and cooling methods can be employed. For example cryogenic cooling using liquid nitrogen cooling lines can be used. Likewise, the solution can be run through propylene glycol heat exchangers to achieve the desired temperature. The chilling time can vary depending on the amount of liquid, the starting temperature and the desired chilled temperature.

Products from the anodic reactions can be effectively transported to the cathode to provide the reactants necessary to form the stable complexes on the cathode surfaces. Maintaining a high degree of homogeneity in the fluids circulated between the catalytic surfaces can also be helpful. A constant flow of about 2-8 $mL/cm^2$ per sec can be used, with typical mesh electrode distances 2 cm apart in large tanks. This flow can be maintained, in part, by the convective flow of gases released from the electrodes during electrolysis.

The mixed solution, chilled or not, can then undergo electrochemical processing through the use of at least one electrode in an electrolyzing step. Each electrode can be or include a conductive metal. Metals can include, but are not limited to copper, aluminum, titanium, rhodium, platinum, silver, gold, iron, a combination thereof or an alloy such as steel or brass. The electrode can be coated or plated with a different metal such as, but not limited to aluminum, gold, platinum or silver. In an embodiment, each electrode is formed of titanium and plated with platinum. The platinum surfaces on the electrodes by themselves can be optimal to catalyze the required reactions. Rough, double layered platinum plating can assure that local "reaction centers" (sharply pointed extrusions) are active and that the reactants not make contact with the underlying electrode titanium substrate.

In one embodiment, rough platinum-plated mesh electrodes in a vertical, coaxial, cylindrical geometry can be optimal, with, for example, not more than 2.5 cm, not more than 5 cm, not more than 10 cm, not more than 20 cm, or not more than 50 cm separation between the anode and cathode. The amperage run through each electrode can be between about 2 amps and about 15 amps, between about 4 amps and about 14 amps, at least about 2 amps, at least about 4 amps, at least about 6 amps, or any range created using any of these values. In one embodiment, 7 amps is used with each electrode.

The amperage can be running through the electrodes for a sufficient time to electrolyze the saline solution. The solution can be chilled during the electrochemical process. The solution can also be mixed during the electrochemical process. This mixing can be performed to ensure substantially complete electrolysis.

Electric fields between the electrodes can cause movement of ions. Negative ions can move toward the anode and positive ions toward the cathode. This can enable exchange of reactants and products between the electrodes. In some embodiments, no barriers are needed between the electrodes.

After amperage has been run through the solution for a sufficient time, an electrolyzed solution is created. The solution can be stored and or tested for particular properties in storage/testing step.

The end products of this electrolytic process can react within the saline solution to produce many different chemical entities. The compositions and composition described herein can include one or more of these chemical entities, known as redox signaling agents or RSAs. RSAs can include, but are not limited to superoxides: $O_2^{*-}$, $HO_2^*$; hypochlorites: $OCl^-$, $HOCl$, $NaOCl$; hypochlorates: $HClO_2$, $ClO_2$, $HClO_3$, $HClO_4$; oxygen derivatives: $O_2$, $O_3$, $O_4^{*-}$, $^1O$; hydrogen derivatives: $H_2$, $H^-$; hydrogen peroxide: $H_2O_2$; hydroxyl free radical: $OH^{*-}$; ionic compounds: $Na^+$, $Cl^-$, $H^+$, $NaCl$, $HCl$, $NaOH$; chlorine: $Cl_2$; water clusters: $n*H_2O$-induced dipolar layers around ions, and combinations thereof. Some RSAs are electron acceptors and include $HOCl$, $NaClO$, $O_2$, $H_2$, $H^+$, $ClO$, $Cl_2$, $H_2O_2$ and some are electron donors and include $O_2^-$, $HO_2$, $Cl^-$, $H^-$, $*OCl$, $O_3$, $*O_2^-$ and $OH^-$.

The chlorine concentration of the electrolyzed solution can be between about 5 ppm and about 34 ppm, between about 10 ppm and about 34 ppm, or between about 15 ppm and about 34 ppm. In one embodiment, the chlorine concentration is about 32 ppm.

In some embodiments, the saline solution includes salt in an amount of 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5, 6, 7, 8, 9, 10, 11, 12, 13, 14, or 15% (w/v), or an amount within a ranged defined by any two of the aforementioned values.

The composition generally can include electrolytic and/or catalytic products of pure saline that mimic redox signaling molecular compositions of the native salt water compounds found in and around human cells. The composition can be fine-tuned to mimic or mirror molecular compositions of different biological media. The composition can have reactive species other than chlorine present. As described, species present in the compositions described herein can include, but are not limited to $O_2$, $H_2$, $Cl_2$, $OCl^-$, $HOCl$, $NaOCl$, $HClO_2$, $ClO_2$, $HClO_3$, $HClO_4$, $H_2O_2$, $Na^+$, $Cl^-$, $H^+$, $H^-$, $OH^-$, $O_3$, $O_4^{*-}$, $^1O_2$, $OH^{*-}$, $HOCl$—$O_2^{*-}$, $HOCl$—$O_3$, $O_2^{*-}$, $HO_2^*$, $NaCl$, $HCl$, $NaOH$, and water clusters: $n*H_2O$-induced dipolar layers around ions, and the like.

As used herein, the term "reactive oxygen species (ROS)" refers to chemically reactive molecules containing oxygen. Examples include ozone, peroxides, active chlorines, active oxygens, superoxides, active hydrogens, hydroxyl radical, and singlet oxygen. ROS are formed as a natural byproduct of the normal metabolism of oxygen and have important roles in cell signaling and homeostasis. ROS can include, but are not limited to superoxides ($O_2^{*-}$, $HO_2^*$), hypochlorites ($OCl^-$, $HOCl$, $NaClO$), hypochlorates ($HClO_2$, $ClO_2$, $HClO_3$, $HClO_4$), oxygen derivatives ($O_2$, $O_3$, $O_4^{*-}$, $O$), hydrogen derivatives ($H_2$, $H^-$), hydrogen peroxide ($H_2O_2$), hydroxyl free radical ($OH^{*-}$), ionic compounds ($Na^+$, $Cl^-$, $H^+$, $OH^-$, $NaCl$, $HCl$, $NaOH$), chlorine ($Cl_2$), water clusters ($n*H_2O$— induced dipolar layers around ions), and combinations thereof. Some ROS can be electron acceptors and some can be electron donors. In some embodiments, a reactive oxygen species is a hypochlorite.

"Hypochlorous acid", as used herein, refers to a weak acid having the chemical formula $HClO$. Hypochlorous acid is also known as chloric (I) acid, chloranol, or hydroxidochlorine. "Hypochlorite" includes ions of hypochlorous acid (for example, $OCl^-$). Salts of hypochlorite are also referred to herein and can include sodium hypochlorite ($NaClO$), calcium hypochlorite ($Ca(ClO)_2$), or potassium hypochlorite ($KClO$). Hypochlorite, or acids and salts thereof, may be present in the gene modulating composition described herein in an amount of 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 1%, 5%, 10%, 15%, 20%, 25%, 30%, 40%, 50%, or greater w/v %, or within a range defined by any two of the aforementioned amounts. In some embodiments, the w/v % of hypochlorite or an acid or salt thereof is 0.072% w/v. In some embodiments, the hypochlorite, or salt or acid thereof, is added directly to a gene modulating composition. In some embodiments, the hypochlorite, or acid or salt thereof, is generated in the gene modulating composition by electrolysis as described herein. In some embodiments, the final amount of hypochlorite is less than, greater than, or equal to about 10, 15, 20, 25, 30, 35, 40, 45, 50, 55, 60, 65, 70, 75, 80, 85, 90, 95, 100, 120, 150, 175, 200, 300 ppm or within a range defined by any two of the aforementioned amounts. In some embodiments, the amount of hypochlorite in the gene modulating composition is between about 50 to about 100 ppm. In some embodiments, the amount of hypochlorite in the gene modulating composition is about 72 ppm.

The gene modulating composition can be bottled in a bottling step. The composition can be bottled in plastic bottles having volumes of 4 ounces to 160 ounces, such as about 4 oz, about 8 oz, about 16 oz, about 32 oz, about 48 oz, about 64 oz, about 80 oz, about 96 oz, about 112 oz, about 128 oz, about 144 oz, about 160 oz, or an amount within a range created using any of these values. The plastic bottles can also be plastic squeezable pouches having similar volumes. In one embodiment, plastic squeezable pouches can have one way valves to prevent leakage of the gene modulating composition.

During bottling, solution from an approved batch can be pumped through a 10 micron filter to remove any larger particles from tanks, dust, hair, etc. that might have found their way into the batch. In the embodiments described above, the filter material may be any suitable material for example metals, glass, fleece, polyester, polypropylene, polyurethane, polytetrafluoroethylene, nylon or any other suitable plastics material. In other embodiments, this filter need not be used. Then, the solution can be pumped into the bottles, the overflow going back into the batch.

Bottles generally may not contain any dyes, metal, or chemicals that can be dissolved by acids or oxidizing agents. Any packaging materials, such as bottles, caps, bottling filters, valves, lines, and heads used can be specifically rated for acids and oxidizing agents. Caps with organic glues, seals, or other components sensitive to oxidation may be avoided, as these could neutralize and weaken the product over time. The compositions provided herein can be filled into suitable packaging such as, for example, tubes, cartons, capsule, jars, bottles, canisters, squeeze pack, pouches, packages, packets, sacks, tank, or other containers.

Packaging materials used herein can aid in preventing decay of free radical species found within the composition. In other embodiments, the bottles and pouches described do not further the decay process. In some embodiments, the bottles and pouches used can be inert with respect to the radical species in the composition. In one embodiment, a container (for example, bottle and/or pouch) can allow less than about 10% decay/month, less than about 9% decay/month, less than about 8% decay/month, less than about 7% decay/month, less than about 6% decay/month, less than about 5% decay/month, less than about 4% decay/month, less than about 3% decay/month, less than about 2% decay/month, less than about 1% decay/month, between about 10% decay/month and about 1% decay/month, between about 5% decay/month and about 1% decay/month, about 10% decay/month, about 9% decay/month, about 8% decay/month, about 7% decay/month, about 6% decay/month, about 5% decay/month, about 4% decay/month, about 3% decay/month, about 2% decay/month, or about 1% decay/month of free radicals in the composition. In one embodiment, a bottle can only result in about 3% decay/month of superoxide. In another embodiment, a pouch can only result in about 4% decay/month of superoxide.

Pulsing potentials in the power supply of the production units can be built into a system for making the composition. Lack of filter capacitors in the rectified power supply can cause the voltages to drop to zero 120 times per second, resulting in a hard spike when the alternating current in the house power lines changes polarity. This hard spike, under Fourier transform, can emit a large bandwidth of frequencies. In essence, the voltage is varying from high potential to zero 120 times a second. In other embodiments, the voltage can vary from high potential to zero about 1,000 times a second, about 500 times a second, about 200 times a second, about 150 times a second, about 120 times a second, about 100 times a second, about 80 times a second, about 50 times a second, about 40 times a second, about 20 times a second, between about 200 times a second and about 20 times a second, between about 150 times a second and about 100 times a second, at least about 100 times a second, at least about 50 times a second, or at least about 120 times a second. This power modulation can allow the electrodes sample all voltages and also provides enough frequency bandwidth to excite resonances in the forming molecules themselves. The time at very low voltages can also provide an environment of low electric fields where ions of similar charge can come within close proximity to the electrodes. All of these factors together can provide a possibility for the formation of stable complexes capable of generating and preserving ROS free radicals.

Waveforms with an alternating current (AC) ripple can be used to provide power to the electrodes. Such an AC ripple can also be referred to as pulse or spiking waveforms and include: any positive pulsing currents such as pulsed waves, pulse train, square wave, saw tooth wave, pulse-width modulation (PWM), pulse duration modulation (PDM), single phase half wave rectified AC, single phase full wave rectified AC or three phase full wave rectified for example.

A bridge rectifier may be used. Other types of rectifiers can be used such as Single-phase rectifiers, Full-wave rectifiers, Three-phase rectifiers, Twelve-pulse bridge, Voltage-multiplying rectifiers, filter rectifier, a silicon rectifier, an SCR type rectifier, a high-frequency (RF) rectifier, an inverter digital-controller rectifier, vacuum tube diodes, mercury-arc valves, solid-state diodes, silicon-controlled rectifiers and the like. Pulsed waveforms can be made with a transistor regulated power supply, a dropper type power supply, a switching power supply and the like.

This pulsing waveform model can be used to stabilize superoxides, hydroxyl radicals and OOH* from many different components and is not limited to any particular variable such as voltage, amps, frequency, flux (current density) or current. The variables are specific to the components used. For example, water and NaCl can be combined which provide molecules and ions in solution. A 60 Hz current can be used, meaning that there are 60 cycles/120 spikes in the voltage (V) per second or 120 times wherein the V is 0 each second. When the V goes down to 0 it is believe that the 0 V allows for ions to drift apart/migrate and reorganize before the next increase in V. Without wishing to be bound by theory, the spiking in V allows for and promotes a variable range of frequencies influencing many different types of compounds and/or ions.

Diodes may also be used. The V may drop to 0 as many times per second as the frequency is adjusted. As the frequency is increased the number of times the V drops is increased.

When the ions are affected by the electricity from the electrodes, they change. While still not wishing to be bound by theory, it is believed that the electricity alters the state of some of the ions/compounds. This alteration results in the pushing of electrons out of their original orbit and/or spin state into a higher energy state and/or a single spin state. This electrolysis provides the energy to form free radicals which are ultimately formed during a multi-generational cycling of reactants and products during the electrolysis process. In other words, compounds and/or ions are initially electrolyzed so that the products that are formed are then themselves reacted with other compounds and/or ions and/or gas to form a second generation of reactants and products. This generational process then happens again so that the products from the second generation react with other compounds and/or ions in solution when the voltage spikes again.

In some embodiments, the redox potential can be about 840 mV. In some embodiments, the frequency can be from about 1 Hz to infinity or to about 100 MHz.

In some embodiments, end products of the electrolytic process can react within the saline solution to produce different chemical entities. The compositions described herein can include one or more of these chemical entities. These end products can include, but are not limited to superoxides: $O_2^{*-}$, $HO_2^*$; hypochlorites: $OCl^-$, $HOCl$, $NaOCl$; hypochlorates: $HClO_2$, $ClO_2$, $HClO_3$, $HClO_4$; oxygen derivatives: $O_2$, $O_3$, $O_4^{*-}$, $^1O$; hydrogen derivatives: $H_2$, $H^-$; hydrogen peroxide: $H_2O_2$; hydroxyl free Radical: $OH^{*-}$; ionic compounds: $Na^+$, $Cl^-$, $H^+$, $OH^-$, $NaCl$, $HCl$, $NaOH$; chlorine: $Cl_2$; and water clusters: $n*H_2O$-induced dipolar layers around ions, several variations.

In order to determine the relative concentrations and rates of production of each of these during electrolysis, certain general chemical principles can be helpful:

1) A certain amount of Gibbs free energy is required for construction of the molecules; Gibbs free energy is proportional to the differences in electrode potentials. Reactions with large energy requirements are less likely to happen, for example an electrode potential of −2.71 V (compared to hydrogen reduction at 0.00 V) is required to make sodium metal: $Na^+ + e^- \rightarrow Na(s)$.

Such a large energy difference requirement makes this reaction less likely to happen compared to other reactions with smaller energy requirements. Electron(s) from the electrodes may be preferentially used in the reactions that require lesser amounts of energy, such as the production of hydrogen gas.

2) Electrons and reactants are required to be at the same micro-locality on the electrodes. Reactions that require several reactants may be less likely to happen, for example: $Cl_2 + 6H_2O \rightarrow 10\ e^- + 2\ ClO_3^- + 12H^+$.

This reaction requires six water molecules and one $Cl_2$ molecule to be at the electrode at the same point at the same time and a release of 10 electrons to simultaneously occur. The probability of this happening generally is smaller than other reactions requiring fewer and more concentrated reactants to coincide, but such a reaction may still occur.

3) Reactants generated in preceding generations can be transported or diffuse to the electrode where reactions happen. For example, dissolved oxygen ($O_2$) produced on the anode from the first generation can be transported to the cathode in order to produce superoxides and hydrogen peroxide in the second generation. Ions can be more readily transported: they can be pulled along by the electric field due to their electric charge. In order for chlorates, to be generated, for example, $HClO_2$ can first be produced to start the cascade, restrictions for $HClO_2$ production can also restrict any subsequent chlorate production. Lower temperatures can prevent $HClO_2$ production.

Stability and concentration of the above products can depend, in some cases substantially, on the surrounding environment. The formation of complexes and water clusters can affect the lifetime of the moieties, especially the free radicals.

In a pH-neutral aqueous solution (pH around 7.0) at room temperature, superoxide free radicals ($O_2^{*-}$) have a half-life of 10's of milliseconds and dissolved ozone ($O_3$) has a half-life of about 20 minutes. Hydrogen peroxide ($H_2O_2$) is relatively long-lived in neutral aqueous environments, but this can depend on redox potentials and UV light. Other entities such as HCl and NaOH rely on acidic or basic environments, respectively, in order to survive. In pH-neutral solutions, $H^+$ and $OH^-$ ions have concentrations of approximately 1 part in 10,000,000 in the bulk aqueous solution away from the electrodes. $H^-$ and $^1O$ can react quickly. The stability of most of these moieties mentioned above can depend on their microenvironment.

Superoxides and ozone can form stable van der Waals molecular complexes with hypochlorites. Clustering of polarized water clusters around charged ions can also have the effect of preserving hypochlorite-superoxide and hypochlorite-ozone complexes. Such complexes can be built through electrolysis on the molecular level on catalytic substrates, and may not occur spontaneously by mixing together components. Hypochlorites can also be produced spontaneously by the reaction of dissolved chlorine gas ($Cl_2$) and water. As such, in a neutral saline solution the formation of one or more of the stable molecules and complexes may exist: dissolved gases: $O_2$, $H_2$, $Cl_2$; hypochlorites: $OCl^-$, HOCl, NaOCl; hypochlorates: $HClO_2$, $ClO_2$, $HClO_3$, $HClO_4$; hydrogen peroxide: $H_2O_2$, ions: $Na^+$, $Cl^-$, $H^+$, $H^-$, $OH^-$; ozone: $O_3$, $O_4^{*-}$; singlet oxygen: $^1O$; hydroxyl free radical: $OH^{*-}$; superoxide complexes: $HOCl-O_2^{*-}$; and ozone complexes: $HOCl-O_3$. One or more of the above molecules can be found within the compositions described herein.

A complete quantum chemical theory can be helpful because production is complicated by the fact that different temperatures, electrode geometries, flows and ion transport mechanisms and electrical current modulations can materially change the relative/absolute concentrations of these components, which could result in producing different distinct compositions. As such, the selection of production parameters can be critical. The amount of time it would take to check all the variations experimentally may be prohibitive.

The chlorine concentration of the electrolyzed solution can be about 5 ppm, about 10 ppm, about 15 ppm, about 20 ppm, about 21 ppm, about 22 ppm, about 23 ppm, about 24 ppm, about 25 ppm, about 26 ppm, about 27 ppm, about 28 ppm, about 29 ppm, about 30 ppm, about 31 ppm, about 32 ppm, about 33 ppm, about 34 ppm, about 35 ppm, about 36 ppm, about 37 ppm, about 38 ppm, less than about 38 ppm, less than about 35 ppm, less than about 32 ppm, less than about 28 ppm, less than about 24 ppm, less than about 20 ppm, less than about 16 ppm, less than about 12 ppm, less than about 5 ppm, between about 30 ppm and about 34 ppm, between about 28 ppm and about 36 ppm, between about 26 ppm and about 38 ppm, between about 20 ppm and about 38 ppm, between about 5 ppm and about 34 ppm, between about 10 ppm and about 34 ppm, or between about 15 ppm and about 34 ppm. In one embodiment, the chlorine concentration is about 32 ppm. In another embodiment, the chlorine concentration is less than about 41 ppm.

The saline concentration in the electrolyzed solution can be about 0.10% w/v, about 0.11% w/v, about 0.12% w/v, about 0.13% w/v, about 0.14% w/v, about 0.15% w/v, about 0.16% w/v, about 0.17% w/v, about 0.18% w/v, about 0.19% w/v, about 0.20% w/v, about 0.30% w/v, about 0.40% w/v, about 0.50% w/v, about 0.60% w/v, about 0.70% w/v, between about 0.10% w/v and about 0.20% w/v, between about 0.11% w/v and about 0.19% w/v, between about 0.12% w/v and about 0.18% w/v, between about 0.13% w/v and about 0.17% w/v, or between about 0.14% w/v and about 0.16% w/v.

The composition generally can include electrolytic and/or catalytic products of pure saline that mimic redox signaling molecular compositions of the native salt water compounds found in and around human cells. The composition can be fine-tuned to mimic or mirror molecular compositions of different biological media. The gene modulating composition can have reactive species other than chlorine present. As described, species present in the compositions described herein can include, but are not limited to $O_2$, $H_2$, $Cl_2$, $OCl^-$, HOCl, NaOCl, $HClO_2$, $ClO_2$, $HClO_3$, $HClO_4$, $H_2O_2$, $Na^+$, $Cl^-$, $H^+$, $H^-$, $OH^-$, $O_3$, $O_4^{*-}$, $^1O$, $OH^{*-}$, $HOCl-O_2^{*-}$, $HOCl-O_3$, $O_2^*$, $HO_2^*$, NaCl, HCl, NaOH, and water clusters: $n^*H_2O$-induced dipolar layers around ions, several variations.

In some embodiments, hydroxyl radicals can be stabilized in the composition by the formation of radical complexes. The radical complexes can be held together by hydrogen bonding. Another radical that can be present in the composition is an OOH* radical. Still other radical complexes can include a nitroxyl-peroxide radical (HNO—HOO*) and/or a hypochlorite-peroxide radical (HOCl—HOO*).

Concentrations of reactive species in the electrolyzed saline solutions, detected by fluorescence photo spectroscopy, may not significantly decrease in time. Mathematical models show that bound $HOCl—*O_2^-$ complexes are possible at room temperature. Molecular complexes can preserve volatile components of reactive species. For example, reactive species concentrations in whole blood as a result of molecular complexes may prevent reactive species degradation over time.

Reactive species can be further divided into "reduced species" (RS) and "reactive oxygen species" (ROS). Reactive species can be formed from water molecules and sodium chloride ions when restructured through a process of forced electron donation. Electrons from lower molecular energy configurations in the salinated water may be forced into higher, more reactive molecular configurations. The species from which the electron was taken can be "electron hungry" and is called the RS and can readily become an electron acceptor (or proton donor) under the right conditions. The species that obtains the high-energy electron can be an electron donor and is called the ROS and may energetically release these electrons under the right conditions.

In some embodiments, the composition can include sodium present at a concentration of 100 to 2500 ppm, including about 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 ppm, or an amount within a range defined by any two of the aforementioned values, with the sodium measured by methods known in the art, including, for example, inductively coupled plasma mass spectrometry (ICP-MS). In yet other embodiments, the composition can include chloride present at a concentration of 0 to 2500 ppm, including about 0, 0.5, 1, 5, 10, 25, 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 ppm, or an amount within a range defined by any two of the aforementioned values, with the chloride measured by methods known in the art, including, for example, inductively coupled plasma mass spectrometry (ICP-MS) or $^{35}Cl$ nuclear magnetic resonance ($^{35}Cl$ NMR). In other embodiments, the composition can include hypochlorous acid present at a concentration of about 10 to about 3000 ppm, including about 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 ppm, or an amount within a range defined by any two of the aforementioned values, with the hypochlorous acid measured by methods known in the art, including, for example, colorimetry or $^{35}Cl$ nuclear magnetic resonance ($^{35}Cl$ NMR). In some embodiments, the composition can include superoxide radical present at a concentration of 10 to 200 µM, including about 10, 20, 30, 40, 50, 60, 70, 75, 80, 85, 90, 91, 92, 93, 94, 95, 96, 97, 98, 99, 100, 110, 120, 130, 140, 150, 160, 170, 180, 190, or 200 µM or an amount within a range defined by any two of the aforementioned values, with the superoxide radical measured by methods known in the art, including, for example, 5-(diisopropoxyphosphoryl)-5-1-pyrroline-N-oxide nuclear magnetic resonance (DIPPMPO-NMR). In other embodiments, the composition can include hydroxyl radical present at a concentration of 0 to 300 µM, including about 0, 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 225, 230, 235, 240, 241, 242, 243, 244, 245, 250, 255, 260, 270, 280, 290, or 300 µM or an amount within a range defined by any two of the aforementioned values, with the hydroxyl radical measured by methods known in the art, including, for example, DIPPMPO-NMR or mass spectrometry (MS). In yet other embodiments, the composition can include no hydroxyl radical.

In yet other embodiments, the composition can have a pH between about 5 and about 9, such as a pH of 5, 5.5, 6, 6.5, 7, 7.1, 7.2, 7.3, 7.4, 7.5, 7.6, 7.7, 7.8, 7.9, 8, 8.5, or 9 or a pH within a range defined by any two of the aforementioned values. In some embodiments, the sodium, chloride, hypochlorous acid, superoxide radical, and hydroxyl radical can be measured less than one year after the composition was made. In some embodiments, the formulation can be administered to a user orally.

The compositions described herein may further include an additive known in the art. In some embodiments, the additive includes a compound that improves the formulation for the mode of administration. In some embodiments, the additive improves the efficacy of the composition. In some embodiments, the additive improves the shelf life of the composition. In some embodiments, the additive is included for aesthetic purposes to improve the appearance, texture, scent, or feel of the composition. Exemplary additives for including in a composition can include moisturizers, humectants, pigments, dyes, pearlescent compounds, nacreous pigments, bismuth oxychloride coated mica, titanium dioxide coated mica, colorants, fragrances, biocides, preservatives, lipolytic agent, diuretics, xanthines (such as caffeine, theophylline, and aminophylline), alpha hydroxy acids, antioxidants, lymphatic drainage agent, antiperspirant agents, exfoliants, hormones, anticellulitic, enzymes, gene expression modulators, medicinal compounds, vitamins, minerals, electrolytes, alcohols, polyols, polypropylene glycol, antiadipogenesis agents, retinoids, retinol, polyisobutene, polyoxyethylene, behenic acid, behenyl, sugar-alcohols, absorbing agents for ultraviolet radiation, botanical extracts, surfactants, silicone oils, organic oils, waxes, alkaline or acidic or buffering agents, film formers, thickening agents, hyaluronic acid, fumed silica, hydrated silica, talc, kaolin, starch, modified starch, mica, nylon, clay, bentonite, organomodified clays, and combinations thereof.

Methods of Modulating Gene Expression

Some embodiments disclosed herein relate to a method of modulating expression of a gene in a cell, including contacting a cell with a gene modulating composition disclosed herein. In some embodiments, a cell can be either isolated or located in situ. When a cell is located in situ, a method may further include administration of a composition to a subject, whereby the composition contacts a cell after administration, and expression of a gene of the cell is thereby modulated.

In some embodiments, a method includes selecting a subject or patient in need. In some embodiments, a patient is selected who is in need of modulation of a gene of interest.

The term "cell" as used herein refers to its meaning as is generally accepted in the art. Cell is used in its usual biological sense, and does not refer to an entire multicellular organism, for example, specifically does not refer to a human being. The cell can be isolated or located in situ in a subject. An "isolated cell" as used herein is a cell or population of cells that have been removed from the environment in which the cell occurs naturally and/or altered or modified from the state in which the cell occurs in its natural environment. An isolated cell can be a cell, for example, in a cell culture. An isolated cell of this invention can also be a cell that can be in an animal and/or introduced into an animal and wherein the cell has been altered or modified. In some embodiments, the cell can be present in situ in an organism, for example, birds, plants and mammals, such as humans, cows, sheep, apes, monkeys, swine, dogs, and cats. The cell can be prokaryotic (for example, bacterial cell) or eukaryotic (for example, mammalian or plant cell). The cell can be of somatic or germ line origin, totipotent or pluripotent, dividing or non-dividing. The cell can also be derived from or can include a gamete or embryo, a stem cell, or a fully differentiated cell.

The term "gene" or "target gene" as used herein refers to their meaning as is generally accepted in the art, and refers to a nucleic acid (for example, DNA or RNA) sequence that includes partial length or entire length coding sequences necessary for the production of a polypeptide. The target gene can also include the UTR or non-coding region of the nucleic acid sequence. A gene or target gene can also encode a functional RNA (fRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA), and/or precursor RNAs thereof. Compositions that modulate gene expression can also be used to manipulate or alter the genotype or phenotype of a subject, organism or cell, by intervening in cellular processes such as genetic imprinting, transcription, translation, or nucleic acid processing (for example, transamination, methylation etc.). The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus.

The term "modulate" as used herein refers to altering the expression of a gene at one of various stages. For example, modulate can refer to when the expression of a gene, or the level of one or more RNA molecules (coding or non-coding), or activity the of one or more RNA molecules or proteins or protein subunits, is up-regulated or down-regulated, such that expression, level, or activity is greater than or less than that observed in the absence of the molecule that effects modulation. For example, the term "modulate" in some embodiments can refer to inhibition and, in other embodiments, can refer to potentiation or up-regulation of gene expression.

As used herein, "gene expression" involves transcription of at least a portion of genomic DNA (for example, at least a portion of a coding region, for example, at least a portion of genomic DNA that encodes a polypeptide) to form RNA (for example, a transcript, or mRNA), which may be translated by ribosomes into a polypeptide (for example, a protein). Assessing gene expression can be done by determining cellular RNA levels or protein levels in a cell.

The terms "inhibit," "down-regulate," or "reduce" as used herein refers to their meanings as generally accepted in the art, and refers to the reduction in the expression of a gene, or in the level of RNA molecules or equivalent RNA molecules encoding one or more proteins or protein subunits, or in the activity of one or more proteins or protein subunits, below that observed in the absence of the gene modulating composition.

The term "up-regulate" as used herein refers to its meaning as is generally accepted in the art, and refers to an increase in either the expression of a gene, or the level of RNA molecules or equivalent RNA molecules encoding one or more proteins or protein subunits, or the activity of one or more RNAs, proteins or protein subunits, above that observed in the absence of the gene modulating composition.

In some embodiments, the expression of the gene is modulated (including either upregulated or downregulated) by between 0.5 fold and 10 fold, or greater, such as 0.5 fold, 0.6 fold, 0.7 fold, 0.8 fold, 0.9 fold, 1 fold, 1.1 fold, 1.2 fold, 1.3 fold, 1.4 fold, 1.5 fold, 1.6 fold, 1.7 fold, 1.8 fold, 1.9 fold, 2 fold, 2.1 fold, 2.2 fold, 2.3 fold, 2.4 fold, 2.5 fold, 2.6 fold, 2.7 fold, 2.8 fold, 2.9 fold, 3 fold, 3.5 fold, 4 fold, 4.5 fold, 5 fold, 6 fold, 7 fold, 8 fold, 9 fold, 10 fold, or greater, or an amount within a range defined by any two of the aforementioned values.

The term "therapeutically effective amount" is used to indicate an amount of a composition that is used to modulate expression of a gene, whether it be upregulation or down-regulation of gene expression. Determination of a therapeutically effective amount is within the capability of those skilled in the art, in view of the disclosure provided herein. The therapeutically effective amount of the composition disclosed herein required as a dose will depend on whether the cell is isolated or in situ, the route of administration, the type of animal, including human, receiving administration, and the physical characteristics of the specific animal under consideration. The dose can be tailored to achieve a desired effect, but will depend on such factors as weight, diet, concurrent medication and other factors which those skilled in the medical arts will recognize. In some embodiments, a dose is provided in an amount of about 0.1 ounce to about 12 ounces, such as 0.1, 0.2, 0.3, 0.4, 0.5, 0.6, 0.7, 0.8, 0.9, 1, 2, 3, 4, 5, 6, 7, 8, 9, 10, 11, or 12 ounces, or an amount within a range defined by any two of the aforementioned values. In some embodiments, the dose is administered at a frequency of four times daily to one time monthly, such as 4 times/day, 3 times/day, 2 times/day, 1 time/day, once every other day, 6 times/week, 5 times/week, 4 times/week, 3 times/week, 2 times/week, 1 time/week, once every other week, twice monthly, or once monthly, or an amount within a range defined by any two of the aforementioned frequencies. In some embodiments, the dose is administered for a period of one day to 10 years or more, for example, for a period of one day, one week, one month, six months, one year, two years, three years, four years, five years, six years, seven years, eight years, nine years, ten years, or more, or within a range defined by any two of the aforementioned values.

In some embodiments, the method of modulating gene expression includes detecting a change in expression of the gene. Various methods for measuring gene expression at the RNA level or protein level are known, including, for example, antibody microarrays, DNA microarrays, tissue microarrays, enzyme linked immunosorbent assays (ELISA), flow cytometry, fluorescence activated cell sorting (FACS), gel electrophoresis, immunofluorescence, immunohistochemistry, immunoprecipitation, mass spectrometry, massively parallel signature sequencing, Northern blot, nuclease protection assays, nucleic acid amplification methods, nucleic acid hybridization techniques, nucleic acid reverse transcription methods, polymerase chain reaction (PCR; including quantitative reverse transcription PCR (qRT-PCR), immune-PCR, and/or differential-display RT-PCR), radioimmunoassay, serial analysis of gene expression, Southern blot, and/or Western blots.

In some embodiments, the gene modulation composition is effective as a stand-alone treatment for modulating gene expression, and as such, is administered alone without other treatments, therapies, or agents for modulating gene expression. In some embodiments, the gene modulation formulation is administered in combination with a therapy for modulating gene expression, such as by use of DNA-binding agents, small molecules (for example, synthetic polyamides), proteins (for example, zinc-finger proteins), RNA interference (RNAi), or synthetic oligonucleotides (for example, triplex-forming oligonucleotides).

In some embodiments, a gene that has modulated expression (or a gene encoding one of the following) includes C-C chemokine receptor type 10 (CCR10), coiled-coil domain-containing protein 126 (CCDC126), DnaJ homolog subfamily C member 3 (DNAJC3), early growth response protein 1 (EGR1), embigin (EMB), immunoglobulin lambda variable 1-41 (IGLV1-41), immunoglobulin lambda variable 1-51 (IGLV1-51), interleukin-1 receptor-associated kinase 3 (IRAK3), potassium channel tetramerization domain containing 12 (KCTD12), pyridine nucleotide-disulfide oxidoreductase domain 1 (PYROXD1), and/or WD repeat-containing protein 11 (WDR11). Additional genes having altered gene expression can include, for example, genes encoding biogenesis of lysosome-related organelles complex 1 subunit 1 (BLOC1S1), calmodulin 2 (CALM2), caspase 4 (CASP4), coiled-coil domain-containing protein 107 (CCDC107), CD63 antigen, coronin actin binding protein 1B (CORO1B), FK506 binding protein 3 (FKBP3), minor histocompatibility antigen H13 (HM13), NEDD4 family interacting protein 1 (NDFIP1), NADH dehydrogenase ubiquinone 1 beta subcomplex subunit 7 (NDUFB7), nuclear factor of kappa light polypeptide gene enhancer in B-cells inhibitor, alpha (NFKBIA), protein of relevant evolutionary and lymphoid interest domain containing 1 (PRELID1), 60S ribosomal protein L27 (RPL27), 60S ribosomal protein L30 (RPL30), translocon-associated protein subunit beta (SSR2), ubiquitin-like protein 5 (UBL5), and/or ubiquinol-cytochrome c reductase, complex III subunit XI (UQCR11).

BLOC1S1 is a component of the ubiquitously expressed BLOC1 multi-subunit protein complex. BLOC1 is required for normal biogenesis of specialized organelles of the endosomal-lysosomal system, such as melanosomes and platelet dense granules.

CALM2 has been shown to interact with a kinase anchor protein 9 and mutations in CALM2 are associated with cardiac arrhythmias.

CASP4 is an enzyme that proteolytically cleaves other proteins at an aspartic acid residue (LEVD-), and belongs to a family of cysteine proteases called caspases. The function of caspase 4 is not fully known, but it is believed to be an inflammatory caspase, along with caspase 1, caspase 5 (and the murine homolog caspase 11), with a role in the immune system.

Coiled-coil domain-containing proteins (such as CCDC126 or CCDC107) are predicted to contain a coiled-coil structure.

Figure 9A:
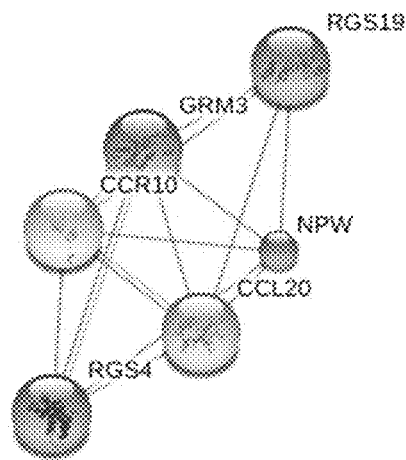
FIGS. 9A-9D show relationship maps of interacting proteins for CCR10 (FIG. 9A), EGR1 (FIG. 9B), IRAK3 (FIG. 9C), and PYROXD1 (FIG. 9D).

CCR10 is the receptor for CCL27 (SCYA27; MIM 604833); CCR10-CCL27 interactions are involved in T cell-mediated skin inflammation. Chemokines are a group of small (approximately 8 to 14 kD), mostly basic, structurally related molecules that regulate cell trafficking of various types of leukocytes through interactions with a subset of 7-transmembrane, G protein-coupled receptors. Chemokines also play fundamental roles in the development, homeostasis, and function of the immune system, and they have effects on cells of the central nervous system as well as on endothelial cells involved in angiogenesis or angiostasis. Chemokines are divided into 2 major subfamilies, CXC and CC, based on the arrangement of the first 2 of the 4 conserved cysteine residues; the 2 cysteines are separated by a single amino acid in CXC chemokines and are adjacent in CC chemokines. Interacting proteins for CCR10 are shown in FIG. 9A.

CD63 antigen is a protein that in humans is encoded by the CD63 gene. CD63 is mainly associated with membranes of intracellular vesicles, although cell surface expression may be induced. The protein encoded by this gene is a member of the transmembrane 4 superfamily, also known as the tetraspanin family. Most of these members are cell-surface proteins that are characterized by the presence of four hydrophobic domains. The proteins mediate signal transduction events that play a role in the regulation of cell development, activation, growth and motility. This encoded protein is a cell surface glycoprotein that is known to complex with integrins. It may function as a blood platelet activation marker. Deficiency of this protein is associated with HermanskyPudlak syndrome. Also this gene has been associated with tumor progression. The use of alternate polyadenylation sites has been found for this gene. Alternative splicing results in multiple transcript variants encoding different proteins.

CORO1B is a protein which in humans is encoded by the CORO1B gene. Members of the coronin family, such as CORO1B, are WD repeat-containing actin-binding proteins that regulate cell motility.

The protein encoded by DNAJC3 contains multiple tetratricopeptide repeat (TPR) motifs as well as the highly conserved J domain found in DNAJ chaperone family members. It is a member of the tetratricopeptide repeat family of proteins and acts as an inhibitor of the interferon-induced, dsRNA-activated protein kinase (PKR).

Figure 9B:
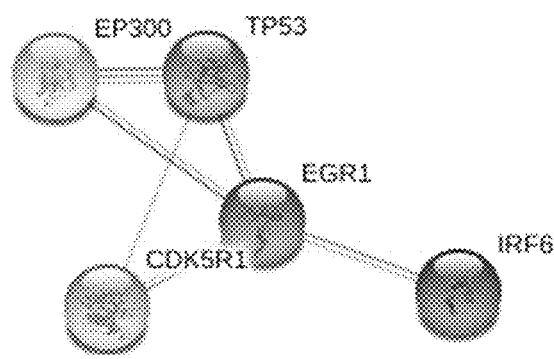

The protein encoded by EGR1 belongs to the EGR family of C2H2-type zinc-finger proteins. It is a nuclear protein and functions as a transcriptional regulator. The products of target genes it activates are required for differentiation and mitogenesis. Studies suggest this is a cancer suppressor gene. Interacting proteins for EGR1 are shown in FIG. 9B.

EMB encodes a transmembrane glycoprotein that is a member of the immunoglobulin superfamily. The encoded protein may be involved in cell growth and development by mediating interactions between the cell and extracellular matrix. A pseudogene of this gene is found on chromosome 1. EMB plays a role in the outgrowth of motoneurons and in the formation of neuromuscular junctions. Diseases associated with EMB include splenic manifestation of leukemia and thymus lymphoma. Among its related pathways are Transport of glucose and other sugars, bile salts and organic acids, metal ions and amine compounds and MAPK-Erk Pathway.

FKBP3 is a member of the immunophilin protein family, which play a role in immunoregulation and basic cellular processes involving protein folding and trafficking. This encoded protein is a cis-trans prolyl isomerase that binds the immunosuppressants FK506 and rapamycin. It has a higher affinity for rapamycin than for FK506 and thus may be an important target molecule for immunosuppression by rapamycin.

HM13 is a nonamer peptide that originates from a protein encoded by the H13 gene. The peptide is generated by the cytosol by the proteasome, enters the endoplasmic reticulum (ER) lumen by the transporter associated with antigen processing (TAP) and is presented on the cell surface on H2-Db major histocompatibility antigen I (MHC I) molecules. The alloreactivity, which leads to transplant rejection in mice, is conferred by Val/Ile polymorphism in the 'SSV (V/I)GVWYL' peptide. The orthologue gene in humans is called HM13. If a related polymorphism exists, and if the HM13 serves as a Minor histocompatibility antigen, however, remains to be addressed.

Immunoglobulin lambda locus genes include IGLV1-41 and IGLV1-51. Immunoglobulins recognize foreign antigens and initiate immune responses such as phagocytosis and the complement system. Each immunoglobulin molecule consists of two identical heavy chains and two identical light chains. There are two classes of light chains, kappa and lambda. This region represents the germline organization of the lambda light chain locus. The locus includes V (variable), J (joining), and C (constant) segments. During B cell development, a recombination event at the DNA level joins a single V segment with a J segment; the C segment is later joined by splicing at the RNA level. Recombination of many different V segments with several J segments provides a wide range of antigen recognition. Additional diversity is attained by junctional diversity, resulting from the random additional of nucleotides by terminal deoxynucleotidyltransferase, and by somatic hypermutation, which occurs during B cell maturation in the spleen and lymph nodes. Several V segments and three C segments are known to be incapable of encoding a protein and are considered pseudogenes. The locus also includes several non-immunoglobulin genes, many of which are pseudogenes or are predicted by automated computational analysis or homology to other species.

Figure 9C:
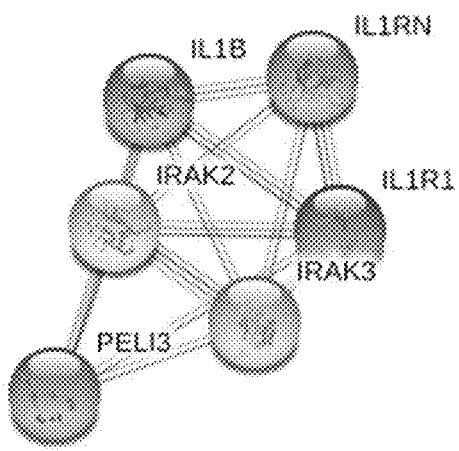

IRAK3 encodes a member of the interleukin-1 receptor-associated kinase protein family. Members of this family are essential components of the Toll/IL-R immune signal transduction pathways. This protein is primarily expressed in monocytes and macrophages and functions as a negative regulator of Toll-like receptor signaling. Mutations in this gene are associated with a susceptibility to asthma. Alternate splicing results in multiple transcript variants. Interacting proteins for IRAK3 are shown in FIG. 9C.

KCTD12 is a protein coding gene. Diseases associated with KCTD12 include Gastrointestinal Stromal Tumor. Among its related pathways are Sweet Taste Signaling and Hepatic ABC Transporters. GO annotations related to this gene include poly(A) RNA binding. An important paralog of this gene is KCTD8. The protein for this gene is Q96CX2-KCD12.

NDUFB7 is an accessory subunit of the multi-subunit NADH:ubiquinone oxidoreductase (complex I) that is not directly involved in catalysis. Mammalian complex I is composed of 45 different subunits. It locates at the mitochondrial inner membrane. This protein complex has NADH dehydrogenase activity and oxidoreductase activity. It transfers electrons from NADH to the respiratory chain. The immediate electron acceptor for the enzyme is believed to be ubiquinone. Alternative splicing occurs at this locus and two transcript variants encoding distinct isoforms have been identified. Initially, NADH binds to Complex I and transfers two electrons to the isoalloxazine ring of the flavin mononucleotide (FMN) prosthetic arm to form FMNH2. The electrons are transferred through a series of iron-sulfur (Fe-S) clusters in the prosthetic arm and finally to coenzyme Q10 (CoQ), which is reduced to ubiquinol (CoQH2). The flow of electrons changes the redox state of the protein, resulting in a conformational change and pK shift of the ionizable side chain, which pumps four hydrogen ions out of the mitochondrial matrix.

NFKBIA is one member of a family of cellular proteins that function to inhibit the NF-κB transcription factor. NFKBIA inhibits NF-κB by masking the nuclear localization signals (NLS) of NF-κB proteins and keeping them sequestered in an inactive state in the cytoplasm. In addition, NFKBIA blocks the ability of NF-κB transcription factors to bind to DNA, which is required for NF-κB's proper functioning.

PRELID1 encodes a member of the late embryogenesis abundant motif-containing protein family. The encoded protein is localized to mitochondria and may function as a cytoprotectant by regulating cell death and differentiation. Alternative splicing results in multiple transcript variants encoding different isoforms. Several related pseudogenes have been identified.

Figure 9D:
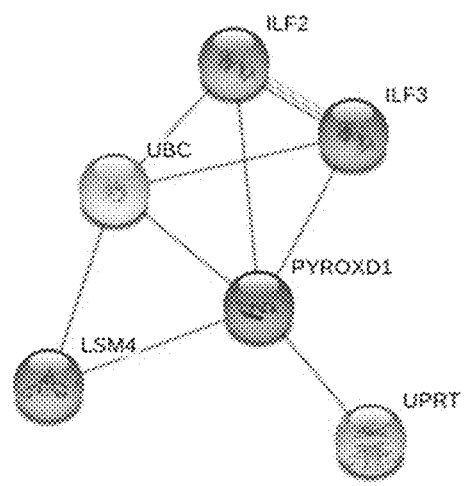

PYROXD1 is a protein coding gene. GO annotations related to this gene include oxidoreductase activity. Interacting proteins for PYROXD1 are shown in FIG. 9D.

RPL27 encodes a ribosomal protein that is a component of the 60S subunit. The protein belongs to the L27E family of ribosomal proteins. It is located in the cytoplasm. As is typical for genes encoding ribosomal proteins, there are multiple processed pseudogenes of this gene dispersed through the genome. Ribosomes, the organelles that catalyze protein synthesis, consist of a small 40S subunit and a large 60Ssubunit. Together these subunits are composed of 4 RNA species and approximately 80 structurally distinct proteins.

RPL30 encodes a ribosomal protein that is a component of the 60S subunit. The protein belongs to the L30E family of ribosomal proteins. It is located in the cytoplasm. This gene is co-transcribed with the U72 small nucleolar RNA gene, which is located in its fourth intron. As is typical for genes encoding ribosomal proteins, there are multiple processed pseudogenes of this gene dispersed through the genome. Ribosomes, the organelles that catalyze protein synthesis, consist of a small 40S subunit and a large 60Ssubunit. Together these subunits are composed of 4 RNA species and approximately 80 structurally distinct proteins.

The signal sequence receptor (SSR) is a glycosylated endoplasmic reticulum (ER) membrane receptor associated with protein translocation across the ER membrane. The SSR consists of 2 subunits, a 34-kD glycoprotein (alpha-SSR or SSR1) and a 22-kD glycoprotein (beta-SSR or SSR2). The human beta-signal sequence receptor gene (SSR2) maps to chromosome bands 1q21-q23.

UBL5 is a protein that in humans is encoded by the UBL5 gene. It has been shown that in *C. elegans* mitochondria treated to lower expression of certain electron transport chain proteins during the L3/L4 stage, its expression levels is higher leading to increased lifespans. Ubiquitin-like proteins (UBLs) are thought to be reversible modulators of protein function rather than protein degraders like ubiquitin.

UQCR11 is made up of 3 exons and is 8,329 base pairs in length. The UQCR11 protein weighs 6.6 kDa and is composed of 56 amino acids. This gene encodes the smallest known component of the ubiquinol-cytochrome c reductase complex, which is also known as Complex III and is part of the mitochondrial respiratory chain. In vertebrates, Complex III contains 11 subunits: 3 respiratory subunits, 2 core proteins and 6 low-molecular weight proteins. Proteobacterial complexes may contain as few as three subunits. UQCR11 protein functions as a binding factor for the iron-sulfur protein in Complex III, which is ubiquitous in human cells. Complex III catalyzes the chemical reaction $QH_2 + 2$ ferricytochrome c $\leftrightarrow$ Q+2 ferrocytochrome c+2H$^+$. Thus, the two substrates of Complex III are dihydroquinone (QH2) and ferri-(Fe$^{3+}$) cytochrome c, whereas its 3 products are quinone (Q), ferro-(Fe$^{2+}$) cytochrome c, and H$^+$. This complex belongs to the family of oxidoreductases, specifically those acting on diphenols and related substances as donor with a cytochrome as acceptor. This enzyme participates in oxidative phosphorylation. It has four cofactors: cytochrome c1, cytochrome b-562, cytochrome b-566 and a 2-Iron ferredoxin of the Rieske type.

WDR11 encodes a member of the WD repeat protein family. WD repeats are minimally conserved regions of approximately 40 amino acids typically bracketed by gly-his and trp-asp (GH-WD), which may facilitate formation of heterotrimeric or multiprotein complexes. Members of this family are involved in a variety of cellular processes, including cell cycle progression, signal transduction, apoptosis, and gene regulation. The gene location suggests that it is a candidate gene for the tumor suppressor locus.

The disclosure is generally described herein using affirmative language to describe the numerous embodiments. The disclosure also includes embodiments in which subject matter is excluded, in full or in part, such as substances or materials, method steps and conditions, protocols, or procedures.

EXAMPLES

Additional alternatives are disclosed in further detail in the following examples, which are not in any way intended to limit the scope of the claims.
General Procedures and Methods
RNA Extraction RNA was collected in a PAXgene blood RNA tube. The RNA was extracted using a PreAnalytiX blood RNA kit and manufacturer's instructions. The RNA samples were analyzed for integrity and concentration using a Bioanalyzer and an Agilent RNA nano 6000 chip and manufacturer's instructions. An estimate of concentration and purity (the A260/A280 absorbance ratio) was determined with UV spectrophotometry.
RNA Concentration After RNA extraction the samples were concentrated by precipitation using ammonium acetate and ethanol. An estimate of concentration and purity (A260/A280 absorbance ratio) was determined with UV spectrophotometry.
RNA Globin Reduction The concentrated sample was further processed using the Ambion GLOBINclear kit and manufacturer's instructions. This kit removes a large percentage of alpha and beta globin RNA that accounts for about 70% of all RNA in whole blood. Removal of this RNA is essential to the success of the array processing so less abundant transcripts are detected.
Prime View Array Processing RNA was prepared for the gene expression arrays using the Affymetrix 3'IVT PLUS Reagent Kit and manufacturer's instructions. The kit generates amplified and biotinylated complementary RNA (cRNA) from poly A RNA in a total RNA sample. The prepared RNA was then hybridized to the Affymetrix Primeview array. Following hybridization the arrays are washed and scanned using Affymetrix equipment and manufacturer's protocols.
Analysis Quality Control analysis was first performed using the Affymetrix Expression Console software. Samples not passing QC metrics were eliminated from the analysis. Samples passing QC analysis were then analyzed using pairwise ANOVA analysis and the Affymetrix Transcriptome Console software. A cutoff of ±2-fold change of expression was used to identify potential candidate genes associated with the use of the product. A Bonferroni corrected p-value of $<1.0 \times 10^{-6}$ would be considered significant.

Example 1

Gene Expression Modulation from Administration of Composition

The following example describes an embodiment showing modulation of gene expression in cells from subjects that were administered a gene modulation composition.

Participants were randomized into test (group A), placebo (group B), or control group (group C) (see FIG. 1). Test group were administered a gene modulation composition. Placebo received water and control group received no composition. Participants completed a health questionnaire and a symptoms log over the course of the study. Participants were 41% male, 59% female, had a mean age of 35 and were 92% Caucasian. RNA was extracted from the blood samples, gene expression levels tested and differential expression within and between groups analyzed. Blood samples were collected from participants at four different time points: time 0, 1 week, 4 weeks and 8 weeks. Gene expression profiles were monitored over the 8-week period to detect any changes in gene expression.

Laboratory data was generated blinded to the group assignment. Differential expression was examined for both time 0 (b2) versus 1 week (wk1) data and time 0 (b2) versus 8-week (wk8) data. RNA was prepared for analysis. In addition to the RNA extraction and analysis, each participant had DNA extracted from collected blood. DNA underwent quantitation.

Venous blood samples were collected at each time point. Total RNA was extracted from each sample using a PreAnalytix PAXgene Blood RNA Kit. After RNA extraction, each sample was concentrated by precipitation to prepare it for a globin reduction assay. The RNA was then subjected to a globin transcript reduction using the Thermo Fisher GLOBINclear kit to prevent interference from excessive globin transcripts, estimated to be as much as 70% of all blood transcripts. Following the globin reduction assay, samples were processed with the Affymetrix GeneChip 3' IVT PLUS kit followed by hybridization to an Affymetrix PrimeView Array that contains 49,395 probe sets across the human genome. The array is analyzed to determine differential expression between time points. Quality control assessment was evaluated and changes in expression levels were evaluated. Genes showing a >±2-fold change in expression over baseline in the test group (group A), and not seen in the placebo group (group B) or in the control group (group C) at >±2-fold change in expression over baseline were identified as potential genes of interest. Additionally, differential expression was examined between group A week 8 and group B week 8 samples. ANOVA was used to test differences between two or more means for analysis of microarray data, to assess the significance of treatment effects, and to select interesting genes based on p-values and fold change. Paired ANOVA was used when comparing within the same study group and unpaired ANOVA when comparing across different study groups. Paired ANOVA compares study subjects at 2 different times (paired observations of the same subject). Unpaired ANOVA compares two different subjects. Genes of interest were further examined for possible pathway connections.

Initially 60 participants were enrolled in the study and randomized into groups (FIG. 1). Participant number 58 did not complete the study, dropping out after the initial blood draw. There were a total of 177 samples collected and processed for RNA extraction on the 59 remaining participants.

Analysis of expression levels were initially conducted using an ANOVA pairwise analysis for baseline (b2) vs. week 1 (wk1). For group A, test group, there were 21 participants (63 samples) for evaluation that had samples that passed QC at both time points. For group B, placebo group, there were 21 participants (63 samples) for evaluation that had samples that passed QC at both time points. For group C, control group, there were there were 10 participants (30 samples) evaluated that had samples that passed QC at both points.

Analysis was also conducted using an ANOVA unpaired analysis for group A week 8 vs. group B week 8. Only samples that passed QC metrics were included in the analysis. For group A, test group, there were 24 samples for evaluation. For group B, placebo group, there were 24 samples for evaluation.

The RNA quality was determined after final preparation for those samples selected for analysis. RNA concentrations and yields of the samples were determined by UV spectrophotometry. An estimate of purity was determined with UV spectrophotometry by measuring the A260/A280 absorbance ratios. A 260/A280 absorbance ratio of >1.7 is desirable although values of <1.7 do not mean that a sample will not perform well in downstream assays. Additionally samples were analyzed on an Agilent 2100 Bioanalyzer using the 2100 expert software (vB.02.07.S153) to estimate integrity by examining the entire electrophoretic trace of the RNA. An estimated RNA Integrity Number (RIN) was generated. RIN numbers of greater than 6 are suggestive of RNA with integrity likely to work in downstream expression analysis. All samples had sufficient yield, 260/280 ratios and estimated RNA integrity numbers to suggest they were suitable for expression analysis. No samples were eliminated from the downstream analysis (Table 1).

TABLE 1

RNA QC Metrics for Tested Samples

| Sample # | Sample ID | ng/µL | 260/280 | Volume (µL) | Yield (ng) | RIN |
|---|---|---|---|---|---|---|
| 1a | RXN001_B2-NG | 53.22 | 1.99 | 30 | 1597 | >8 |
| 1b | RXN001_WK1-NG | 43.87 | 1.87 | 30 | 1316 | >8 |
| 1c | RXN001_wk8 | 65.14 | 1.87 | 30 | 1954 | >8 |
| 2a | RXN002_B2-NG | 40.59 | 1.83 | 30 | 1218 | >8 |
| 2b | RXN002_WK1-NG | 63.54 | 1.92 | 30 | 1906 | >8 |
| 2c | RXN002_wk8 | 69.84 | 1.87 | 30 | 2095 | >8 |
| 3a | RXN003_B2-NG | 59.18 | 1.97 | 30 | 1775 | >8 |
| 3b | RXN003_WK1-NG | 68.61 | 1.94 | 30 | 2058 | >8 |
| 3c | RXN003_wk8 | 133.06 | 1.99 | 30 | 3992 | >8 |
| 4a | RXN004_B2-NG | 45.57 | 1.92 | 30 | 1367 | >8 |
| 4b | RXN004_wk1 | 99 | 2.08 | 14 | 1386 | >8 |
| 4c | RXN004_wk8 | 44.21 | 1.72 | 30 | 1326 | >8 |
| 5a | RXN005_B2-NG | 42.97 | 1.87 | 30 | 1289 | >8 |
| 5b | RXN005_WK1-NG | 34.32 | 1.87 | 30 | 1030 | >8 |
| 5c | RXN005_wk8 | 68.34 | 1.93 | 30 | 2050 | >8 |
| 6a | RXN006_B2-NG | 63.04 | 2.04 | 30 | 1891 | >8 |
| 6b | RXN006_WK1-NG | 28.77 | 1.93 | 30 | 863 | >8 |
| 6c | RXN006_wk8 | 53.18 | 1.86 | 30 | 1595 | >8 |
| 7a | RXN007_B2-NG | 54.9 | 1.96 | 30 | 1647 | >8 |
| 7b | RXN007_WK1-NG | 31.09 | 1.74 | 30 | 933 | >8 |
| 7c | RXN007_wk8 | 100.52 | 1.96 | 30 | 3016 | >8 |
| 8a | RXN008_B2-NG | 46.46 | 1.88 | 30 | 1394 | >8 |
| 8b | RXN008_WK1-NG | 40.29 | 1.9 | 30 | 1209 | >8 |
| 8c | RXN008_wk8 | 170.61 | 2.04 | 30 | 5118 | >8 |
| 9a | RXN009_B2-NG | 25.66 | 1.81 | 30 | 770 | >8 |
| 9b | RXN009_WK1-NG | 25.51 | 1.91 | 30 | 765 | >8 |
| 9c | RXN009_wk8 | 57.39 | 1.83 | 30 | 1722 | >8 |
| 10a | RXN010_B2-NG | 35.44 | 1.94 | 30 | 1063 | >8 |
| 10b | RXN010_WK1-NG | 15.31 | 1.72 | 30 | 459 | >8 |
| 10c | RXN010_wk8 | 50.09 | 1.82 | 30 | 1503 | >8 |
| 11a | RXN011_B2-NG | 51.01 | 1.94 | 30 | 1530 | >8 |
| 11b | RXN011_wk4 | 66 | 2.02 | 14 | 924 | >8 |
| 11c | RXN011_wk8 | 86.61 | 1.94 | 30 | 2598 | >8 |
| 12a | RXN012_B2-NG | 54.55 | 2.03 | 30 | 1637 | >8 |
| 12b | RXN012_WK1-NG | 30.94 | 1.79 | 30 | 928 | >8 |
| 12c | RXN012_wk8 | 70.85 | 1.9 | 30 | 2126 | >8 |
| 13a | RXN013_B2-NG | 32.75 | 1.76 | 30 | 983 | >8 |
| 13b | RXN013_WK1-NG | 18.62 | 1.73 | 30 | 559 | >8 |
| 13c | RXN013_wk8 | 94.14 | 1.96 | 30 | 2824 | >8 |
| 14a | RXN014_B2-NG | 54.89 | 1.92 | 30 | 1647 | >8 |
| 14b | RXN014_WK1-NG | 17.89 | 1.73 | 30 | 537 | >8 |
| 14c | RXN014_wk8 | 69.33 | 1.83 | 30 | 2080 | >8 |
| 15a | RXN015_B2-NG | 29.58 | 1.84 | 30 | 887 | >8 |
| 15b | RXN015_WK1-NG | 21.34 | 1.73 | 30 | 640 | >8 |
| 15c | RXN015_wk8 | 33.91 | 1.8 | 30 | 1017 | >8 |
| 16a | RXN016_B2-NG | 56.65 | 1.96 | 30 | 1700 | >8 |
| 16b | RXN016_WK1-NG | 28.19 | 1.79 | 30 | 846 | >8 |
| 16c | RXN016_wk8 | 66.57 | 1.92 | 30 | 1997 | >8 |
| 17a | RXN017_B2-NG | 20.44 | 1.53 | 30 | 613 | >8 |
| 17b | RXN017_wk1 | 100.704 | 1.99 | 30 | 3021 | >8 |
| 17c | RXN017_wk8 | 157.96 | 2.02 | 30 | 4739 | >8 |
| 18a | RXN018_B2-NG | 25.72 | 1.76 | 30 | 772 | >8 |
| 18b | RXN018_wk4 | 60 | 1.94 | 14 | 840 | >8 |
| 18c | RXN018_wk8 | 97.04 | 1.97 | 30 | 2911 | >8 |
| 19a | RXN019_B2-NG | 42.59 | 1.96 | 30 | 1278 | >8 |
| 19b | RXN019_wk1 | 43.88 | 1.89 | 30 | 1316 | >8 |
| 19c | RXN019_wk8 | 45.78 | 1.82 | 30 | 1373 | >8 |
| 20a | RXN020_B2-NG | 28.12 | 1.77 | 30 | 844 | >8 |
| 20b | RXN020_wk1 | 40.304 | 1.87 | 30 | 1209 | >8 |
| 20c | RXN020_wk8 | 55.91 | 1.79 | 30 | 1677 | >8 |
| 21a | RXN021_B2-NG | 47.85 | 1.93 | 30 | 1436 | >8 |
| 21b | RXN021_wk1 | 56.824 | 2.01 | 30 | 1705 | >8 |
| 21c | RXN021_wk8 | 155.98 | 2.02 | 30 | 4679 | >8 |
| 22a | RXN022_B2-NG | 53.36 | 2 | 30 | 1601 | >8 |
| 22b | RXN022_wk1 | 38.104 | 1.84 | 30 | 1143 | >8 |
| 22c | RXN022_wk8 | 179.66 | 1.99 | 30 | 5390 | >8 |
| 23a | RXN023_B2-NG | 54.02 | 1.92 | 30 | 1621 | >8 |
| 23b | RXN023_wk1 | 30.016 | 1.87 | 30 | 900 | >8 |
| 23c | RXN023_wk8 | 35.49 | 1.72 | 30 | 1065 | >8 |
| 24a | RXN024_B2-NG | 44.79 | 1.81 | 30 | 1344 | >8 |
| 24b | RXN024_wk1 | 54.584 | 1.95 | 30 | 1638 | >8 |
| 24c | RXN024_wk8 | 103.68 | 1.95 | 30 | 3110 | >8 |
| 25a | RXN025_B2-NG | 115.67 | 2.03 | 30 | 3470 | >8 |
| 25b | RXN025_wk4 | 150 | 2.09 | 14 | 2100 | >8 |
| 25c | RXN025_wk8 | 56.44 | 1.87 | 30 | 1693 | >8 |
| 26a | RXN026_B2-NG | 73.93 | 2.03 | 30 | 2218 | >8 |
| 26b | RXN026_wk1 | 59.464 | 1.94 | 30 | 1784 | >8 |
| 26c | RXN026_wk8 | 90.19 | 1.95 | 30 | 2706 | >8 |
| 27a | RXN027_B2-NG | 46.09 | 2 | 30 | 1383 | >8 |
| 27b | RXN027_wk1 | 54.12 | 1.94 | 30 | 1624 | >8 |
| 27c | RXN027_wk8 | 32.6 | 1.67 | 30 | 978 | >8 |
| 28a | RXN028_B2-NG | 54.56 | 2.04 | 30 | 1637 | >8 |
| 28b | RXN028_wk1 | 47.888 | 1.85 | 30 | 1437 | >8 |
| 28c | RXN028_wk8 | 51.53 | 1.82 | 30 | 1546 | >8 |
| 29a | RXN029_B2-NG | 69.33 | 2.06 | 30 | 2080 | >8 |
| 29b | RXN029_wk1 | 52.192 | 1.92 | 30 | 1566 | >8 |
| 29c | RXN029_wk8 | 68.59 | 1.96 | 30 | 2058 | >8 |
| 30a | RXN030_B2-NG | 31.18 | 1.82 | 30 | 935 | >8 |
| 30b | RXN030_wk1 | 27.088 | 1.74 | 30 | 813 | >8 |
| 30c | RXN030_wk8 | 30.22 | 1.57 | 30 | 907 | >8 |
| 31a | RXN031_b2 | 36.2 | 1.83 | 30 | 1086 | >8 |
| 31b | RXN031_wk1 | 25.99 | 1.66 | 30 | 780 | >8 |
| 31c | RXN031_wk8 | 128.2 | 2.02 | 30 | 3846 | >8 |
| 32a | RXN032_b2 | 42.744 | 1.9 | 30 | 1282 | >8 |
| 32b | RXN032_wk4 | 156 | 2.08 | 14 | 2184 | >8 |
| 32c | RXN032_wk8 | 76.99 | 1.93 | 30 | 2310 | >8 |
| 33a | RXN033_b2 | 38.14 | 1.87 | 30 | 1144 | >8 |
| 33b | RXN033_wk1 | 76.21 | 1.98 | 30 | 2286 | >8 |
| 33c | RXN033_wk8 | 167.73 | 2.07 | 30 | 5032 | >8 |
| 34a | RXN034_b2 | 68.87 | 1.9 | 30 | 2066 | >8 |
| 34b | RXN034_wk1 | 42.75 | 1.94 | 30 | 1283 | >8 |
| 34c | RXN034_wk8 | 48.42 | 1.83 | 30 | 1453 | >8 |
| 35a | RXN035_b2 | 41.74 | 1.85 | 30 | 1252 | >8 |
| 35b | RXN035_wk1 | 43.544 | 1.89 | 30 | 1306 | >8 |
| 35c | RXN035_wk8 | 45.54 | 1.97 | 30 | 1366 | >8 |
| 36a | RXN036_b2 | 76.92 | 1.91 | 30 | 2308 | >8 |
| 36b | RXN036_wk1 | 22.848 | 1.95 | 30 | 685 | >8 |
| 36c | RXN036_wk8 | 73.61 | 1.97 | 30 | 2208 | >8 |
| 37a | RXN037_b2 | 20.43 | 1.66 | 30 | 613 | >8 |
| 37b | RXN037_wk1 | 56.64 | 2.04 | 30 | 1699 | >8 |
| 37c | RXN037_wk8 | 53.21 | 1.82 | 30 | 1596 | >8 |
| 38a | RXN038_b2 | 19.13 | 1.77 | 30 | 574 | >8 |
| 38b | RXN038_wk1 | 32.808 | 1.77 | 30 | 984 | >8 |
| 38c | RXN038_wk8 | 32.27 | 1.76 | 30 | 968 | >8 |
| 39a | RXN039_b2 | 65.82 | 1.94 | 30 | 1975 | >8 |
| 39b | RXN039_wk4 | 116 | 2.06 | 14 | 1624 | >8 |
| 39c | RXN039_wk8 | 35.12 | 1.77 | 30 | 1054 | >8 |
| 40a | RXN040_b2 | 53.57 | 1.97 | 30 | 1607 | >8 |
| 40b | RXN040_wk1 | 27.256 | 1.85 | 30 | 818 | >8 |
| 40c | RXN040_wk8 | 55.62 | 1.83 | 30 | 1669 | >8 |
| 41a | RXN041_b2 | 55.96 | 1.9 | 30 | 1679 | >8 |
| 41b | RXN041_wk1 | 25.112 | 1.83 | 30 | 753 | >8 |
| 41c | RXN041_wk8 | 18.22 | 1.63 | 30 | 547 | >8 |
| 42a | RXN042_b2 | 53.05 | 1.87 | 30 | 1592 | >8 |

TABLE 1-continued

RNA QC Metrics for Tested Samples

| Sample # | Sample ID | ng/μL | 260/280 | Volume (μL) | Yield (ng) | RIN |
|---|---|---|---|---|---|---|
| 42b | RXN042_wk1 | 39.592 | 2.03 | 30 | 1188 | >8 |
| 42c | RXN042_wk8 | 108.63 | 2.04 | 30 | 3259 | >8 |
| 43a | RXN043_b2 | 23.44 | 1.86 | 30 | 703 | >8 |
| 43b | RXN043_wk1 | 28.616 | 1.75 | 30 | 858 | >8 |
| 43c | RXN043_wk8 | 113.75 | 2.03 | 30 | 3413 | >8 |
| 44a | RXN044_b2 | 27.31 | 1.75 | 30 | 819 | >8 |
| 44b | RXN044_wk1 | 29.152 | 1.82 | 30 | 875 | >8 |
| 44c | RXN044_wk8 | 30.63 | 1.67 | 30 | 919 | >8 |
| 45a | RXN045_b2 | 54.26 | 1.93 | 30 | 1628 | >8 |
| 45b | RXN045_wk1 | 36.656 | 1.76 | 30 | 1100 | >8 |
| 45c | RXN045_wk8 | 35.47 | 1.78 | 30 | 1064 | >8 |
| 46a | RXN046_b2 | 64.51 | 1.93 | 30 | 1935 | >8 |
| 46b | RXN046_wk4 | 167 | 2.07 | 14 | 2338 | >8 |
| 46c | RXN046_wk8 | 71.09 | 1.9 | 30 | 2133 | >8 |
| 47a | RXN047_b2 | 40.44 | 1.94 | 30 | 1213 | >8 |
| 47b | RXN047_wk1 | 72.544 | 2.04 | 30 | 2176 | >8 |
| 47c | RXN047_wk8 | 200.38 | 2.08 | 30 | 6011 | >8 |
| 48a | RXN048_b2 | 23.76 | 1.76 | 30 | 713 | >8 |
| 48b | RXN048_wk1 | 51.416 | 1.92 | 30 | 1542 | >8 |
| 48c | RXN048_wk8 | 52.48 | 1.79 | 30 | 1574 | >8 |
| 49a | RXN049_b2 | 28.928 | 1.82 | 30 | 868 | >8 |
| 49b | RXN049_wk1 | 52.968 | 2.01 | 30 | 1589 | >8 |
| 49c | RXN049_wk8 | 101.51 | 1.99 | 30 | 3045 | >8 |
| 50a | RXN050_b2 | 40.552 | 1.81 | 30 | 1217 | >8 |
| 50b | RXN050_wk1 | 36.56 | 1.81 | 30 | 1097 | >8 |
| 50c | RXN050_wk8 | 78.27 | 1.94 | 30 | 2348 | >8 |
| 51a | RXN051_b2 | 101.232 | 1.98 | 30 | 3037 | >8 |
| 51b | RXN051_wk1 | 27.52 | 1.8 | 30 | 826 | >8 |
| 51c | RXN051_wk8 | 78.5 | 1.95 | 30 | 2355 | >8 |
| 52a | RXN052_b2 | 31.92 | 1.72 | 30 | 958 | >8 |
| 52b | RXN052_wk1 | 38.88 | 1.88 | 30 | 1166 | >8 |
| 52c | RXN052_wk8 | 60.19 | 1.89 | 30 | 1806 | >8 |
| 53a | RXN053_b2 | 38.664 | 1.9 | 30 | 1160 | >8 |
| 53b | RXN053_wk4 | 128 | 2.07 | 14 | 1792 | >8 |
| 53c | RXN053_wk8 | 66.63 | 1.82 | 30 | 1999 | >8 |
| 54a | RXN054_b2 | 64.856 | 1.91 | 30 | 1946 | >8 |
| 54b | RXN054_wk1 | 36.216 | 1.84 | 30 | 1086 | >8 |
| 54c | RXN054_wk8 | 46.07 | 1.86 | 30 | 1382 | >8 |
| 55a | RXN055_b2 | 31.088 | 1.9 | 30 | 933 | >8 |
| 55b | RXN055_wk1 | 61.4 | 2.01 | 30 | 1842 | >8 |
| 55c | RXN055_wk8 | 46.77 | 1.82 | 30 | 1403 | >8 |
| 56a | RXN056_b2 | 24.776 | 1.78 | 30 | 743 | >8 |
| 56b | RXN056_wk1 | 59.592 | 2.02 | 30 | 1788 | >8 |
| 56c | RXN056_wk8 | 84.5 | 1.91 | 30 | 2535 | >8 |
| 57a | RXN057_b2 | 34.232 | 1.85 | 30 | 1027 | >8 |
| 57b | RXN057_wk1 | 43.792 | 1.98 | 30 | 1314 | >8 |
| 57c | RXN057_wk8 | 80.76 | 1.99 | 30 | 2423 | >8 |
| 59a | RXN059_b2 | 27.136 | 2.18 | 30 | 814 | >8 |
| 59b | RXN059_wk4 | 139 | 2.1 | 14 | 1946 | >8 |
| 59c | RXN059_wk8 | 184.79 | 2.07 | 30 | 5544 | >8 |
| 60a | RXN060_b2 | 17.768 | 1.81 | 30 | 533 | >8 |
| 60b | RXN060_wk4 | 45 | 1.97 | 14 | 630 | >8 |
| 60c | RXN060_wk8 | 33.57 | 1.71 | 30 | 1007 | >8 |

Figure 2A:
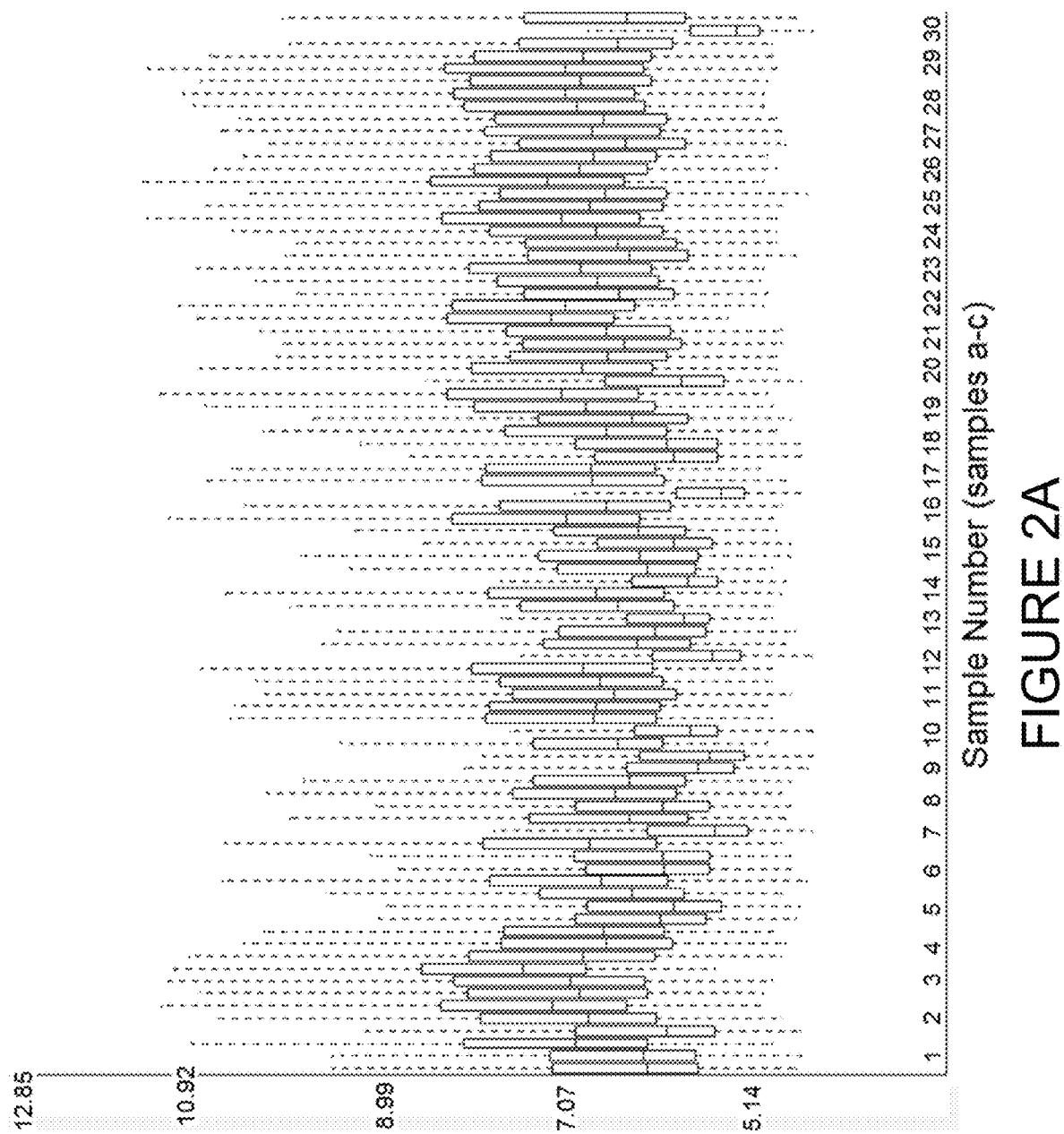
FIGS. 2A and 2B graphically depicts certain embodiments of a log probe cell intensity box plot showing the average log transformed probe intensity (y-axis) for each sample (x-axis) across 49372 probes for each experiment. Each sample along the x-axis includes three cell intensity box plots: at baseline, at week 1, and at week 8 (left to right). Table 1, included herein, further describes each sample.
Figure 2B:
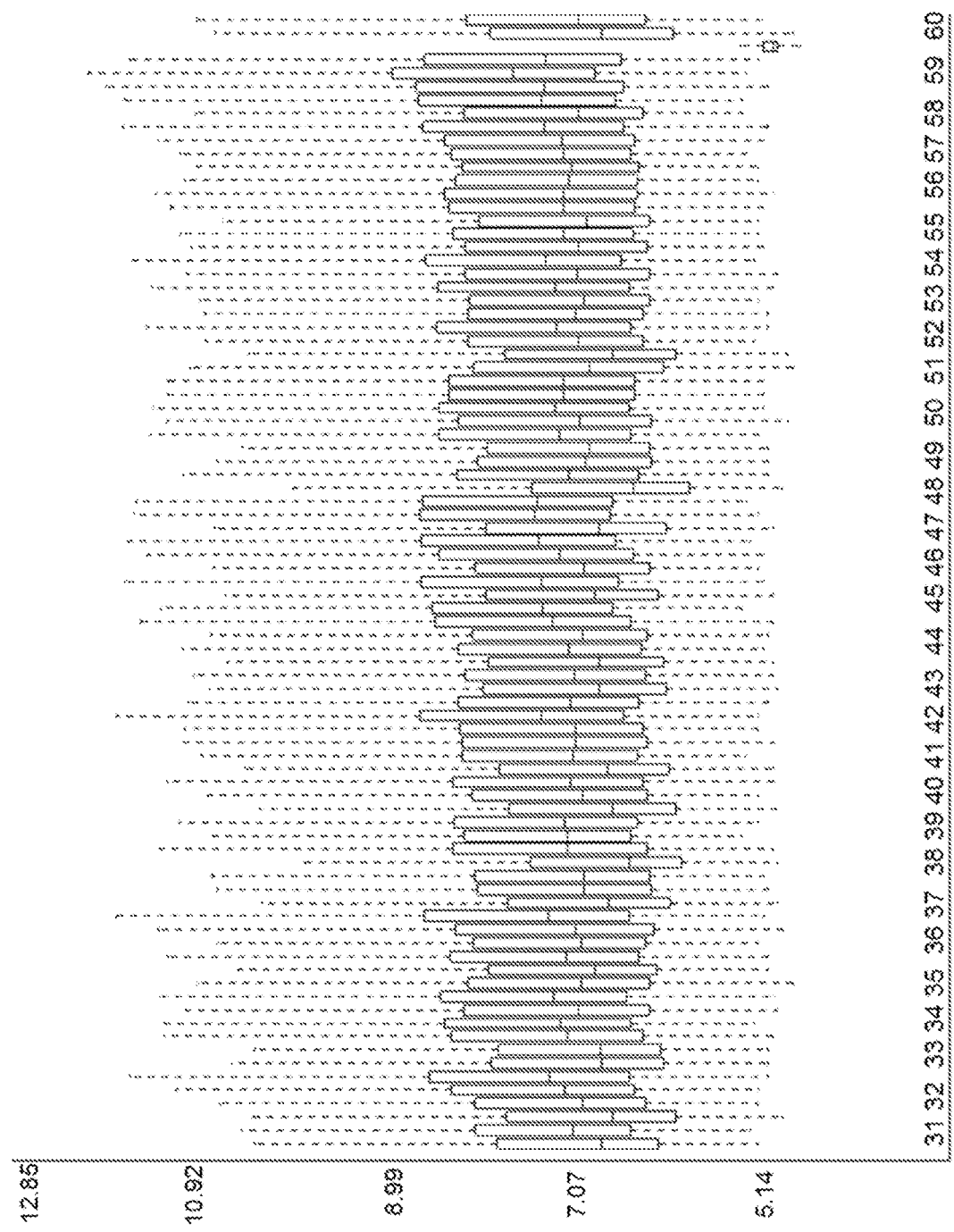

Using the Expression Console software a log probe cell intensity box plot was generated (FIGS. 2A-2B). The probe cell intensity creates a box plot of the probe intensity values for each array. Probe cell intensities are prior to analysis/summarization and have not been normalized; therefore, some differences in the distributions are to be expected. The plot compares the distribution of intensities on each array to the median probe intensity value for the group. Divergent probe intensity distributions relative to the other arrays may indicate that a sample should be eliminated from the analysis. Probe intensity was generally similar across samples at all time points implying minimal stratification from the experiments. Although some samples, such as RXN012_wk1, had lower median probe intensity values, the median fell within the distribution of the other samples and these samples continued in the analysis.

Additional QC analysis of sample performance was completed with the Expression Console software. The microarrays contain hybridization, labeling, and housekeeping gene controls. Samples not passing manufacture recommended thresholds for multiple controls were eliminated from the analysis.

Figure 3A:
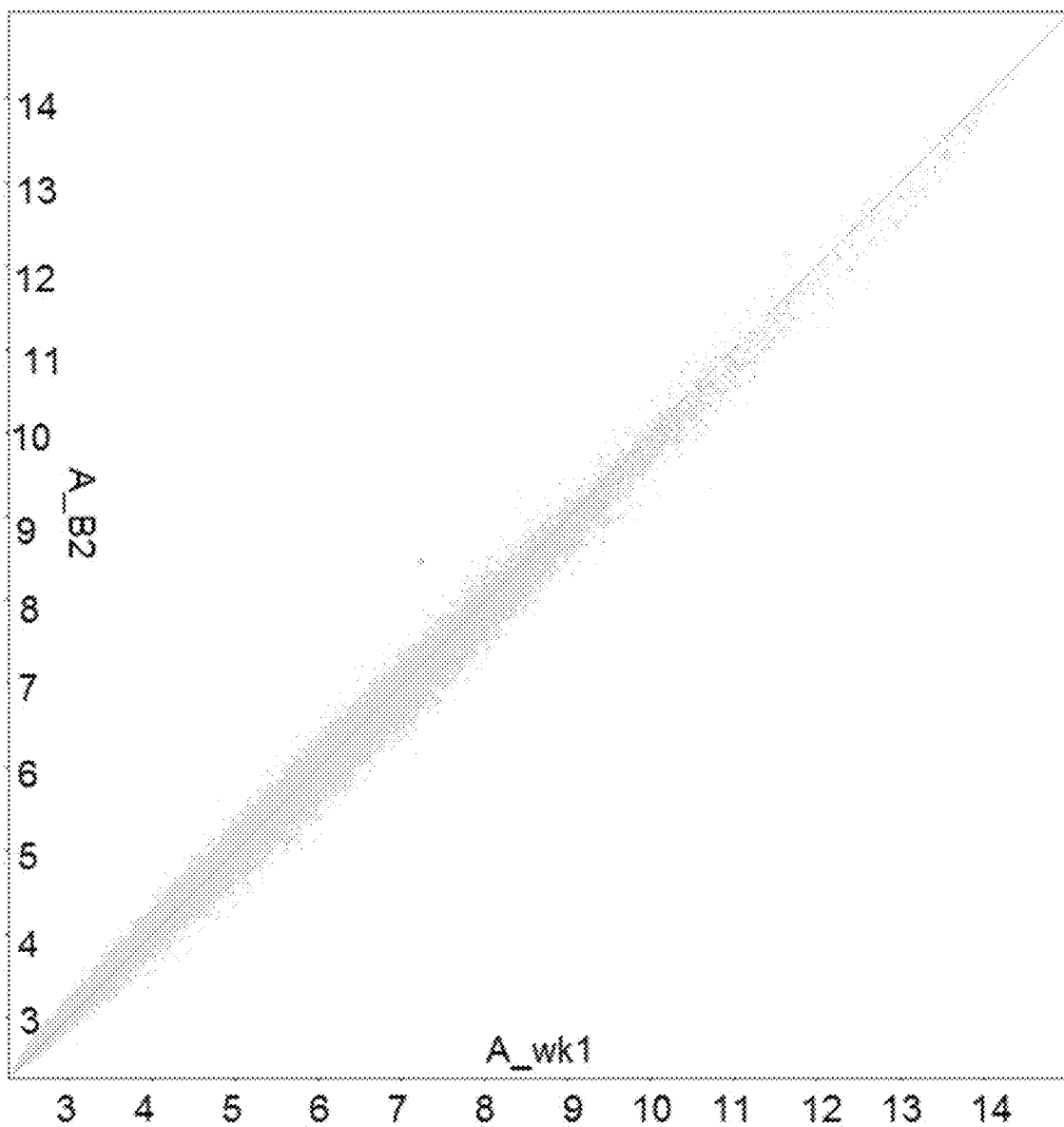
FIGS. 3A-3C graphically depict a ±2-fold change in gene expression in subjects of group A (FIG. 3A—test), group B (FIG. 3B—placebo), and group C (FIG. 3C—control) at baseline (y-axis) verses week 1 (x-axis) following exposure to group treatment. Outliers above the median represent probe sets upregulated by greater than 2-fold. Outliers below the median represent probes sets downregulated by greater than 2-fold.
Figure 3B:
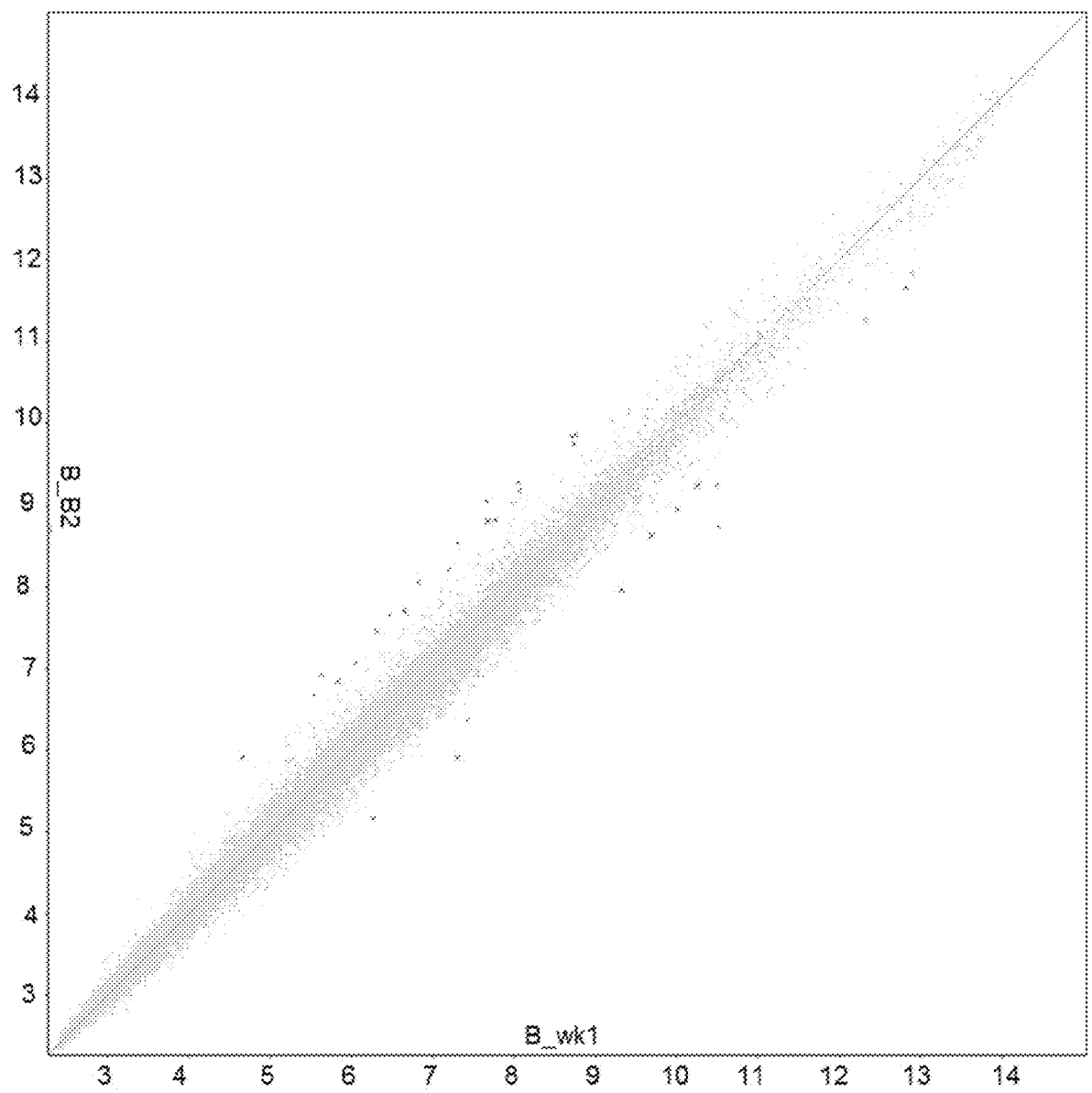
Figure 3C:
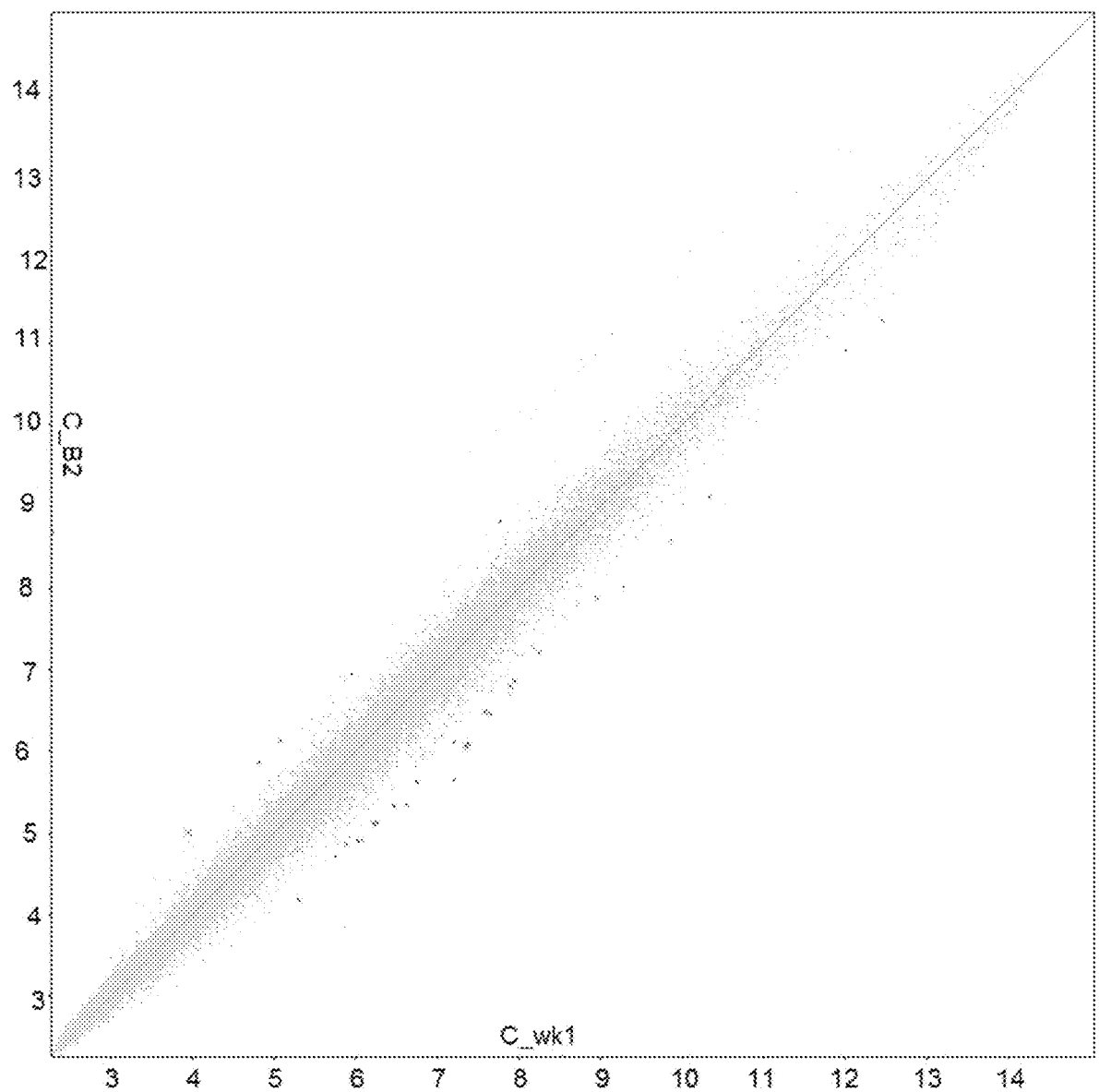

Based on analysis of 49372 probe sets, only one probe set showed a greater than 2-fold change in expression in the test group (A) when comparing group A_b2 versus group A wk1 differential expression. The only gene showing change at this level was also seen in the placebo group at similar levels. FIG. 3A is a scatter plot of this differential expression. Although there were changes observed in the placebo group (FIG. 3B) these are likely random variation as none of the expression changes reached a significant Bonferroni corrected p-value ($<1.0\times10^{-6}$) and many did not reach a significant false detection rate (FDR) p-value ($<0.05$). The Bonferroni p-value, although very stringent, is generally accepted as the gold standard in assays with multiple tests. The control group had the most significant changes (FIG. 3C) with one probe meeting a significant value. This is likely random variation and may be attributed to the small sample size in this group.

There are two major possibilities for what was observed in the data. First, there could be no effect on expression in the genes tested when there is exposure to the product. Second, due to the short timeframe, 1 week of consumption of the product or placebo, there may have not been enough time for biological changes in expression to occur. A third possibility is that smaller changes of less than two-fold may be occurring, although this may not be statistically significant.

Changes in expression may take a significant time to occur and the 8-week sample comparison would guide whether a future study would need to have a longer time trial, or whether there are significant changes after the 8 week exposure to the product. Based on these observations evaluating differential expression of the baseline versus 8-week samples was completed.

Figure 4:
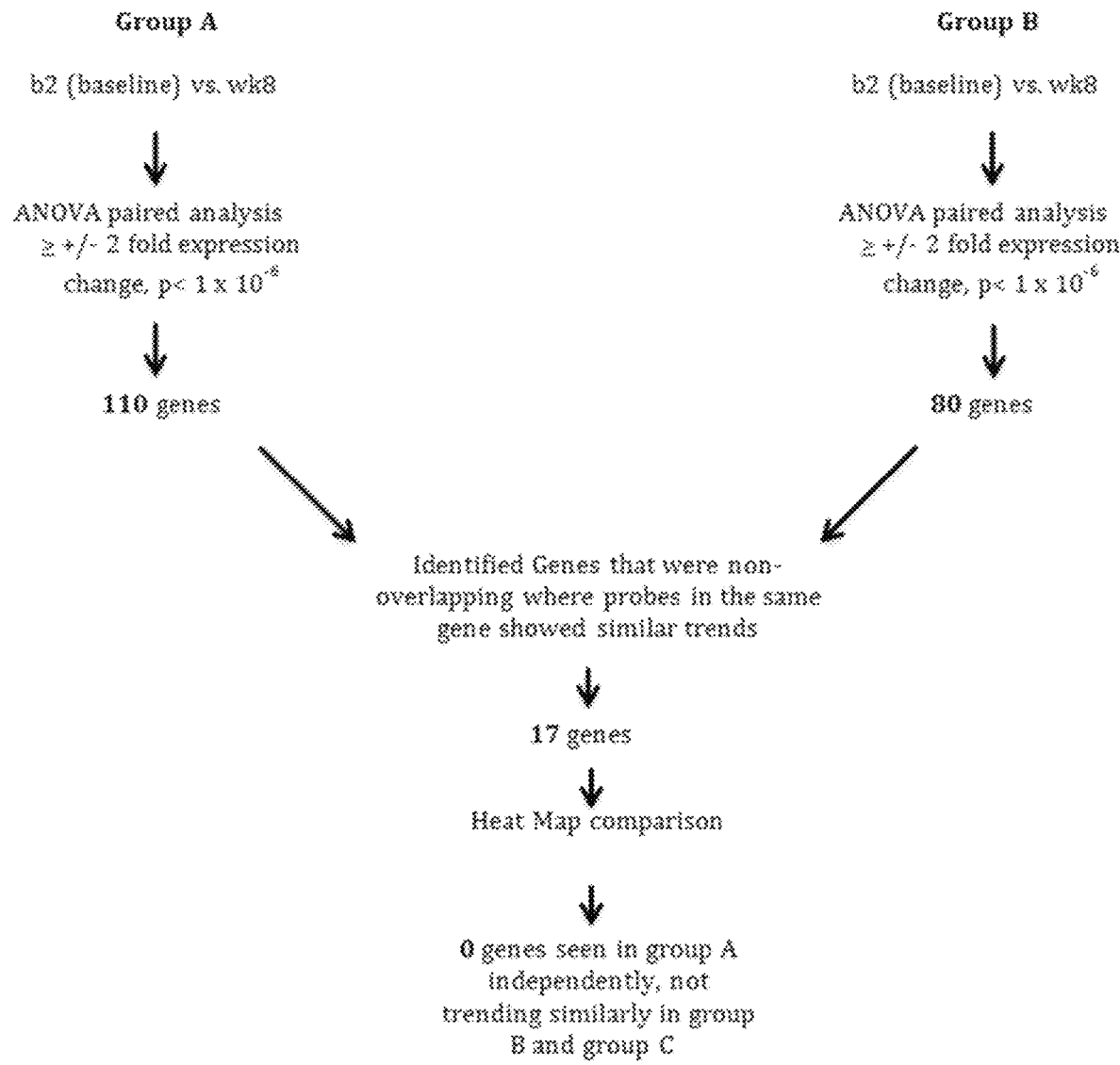
FIG. 4 depicts a schematic representation of certain embodiments showing experimental design for subjects in group A (test group) and group B (placebo) for identification of gene expression at baseline compared to 8 weeks after treatment.
Figure 5A:
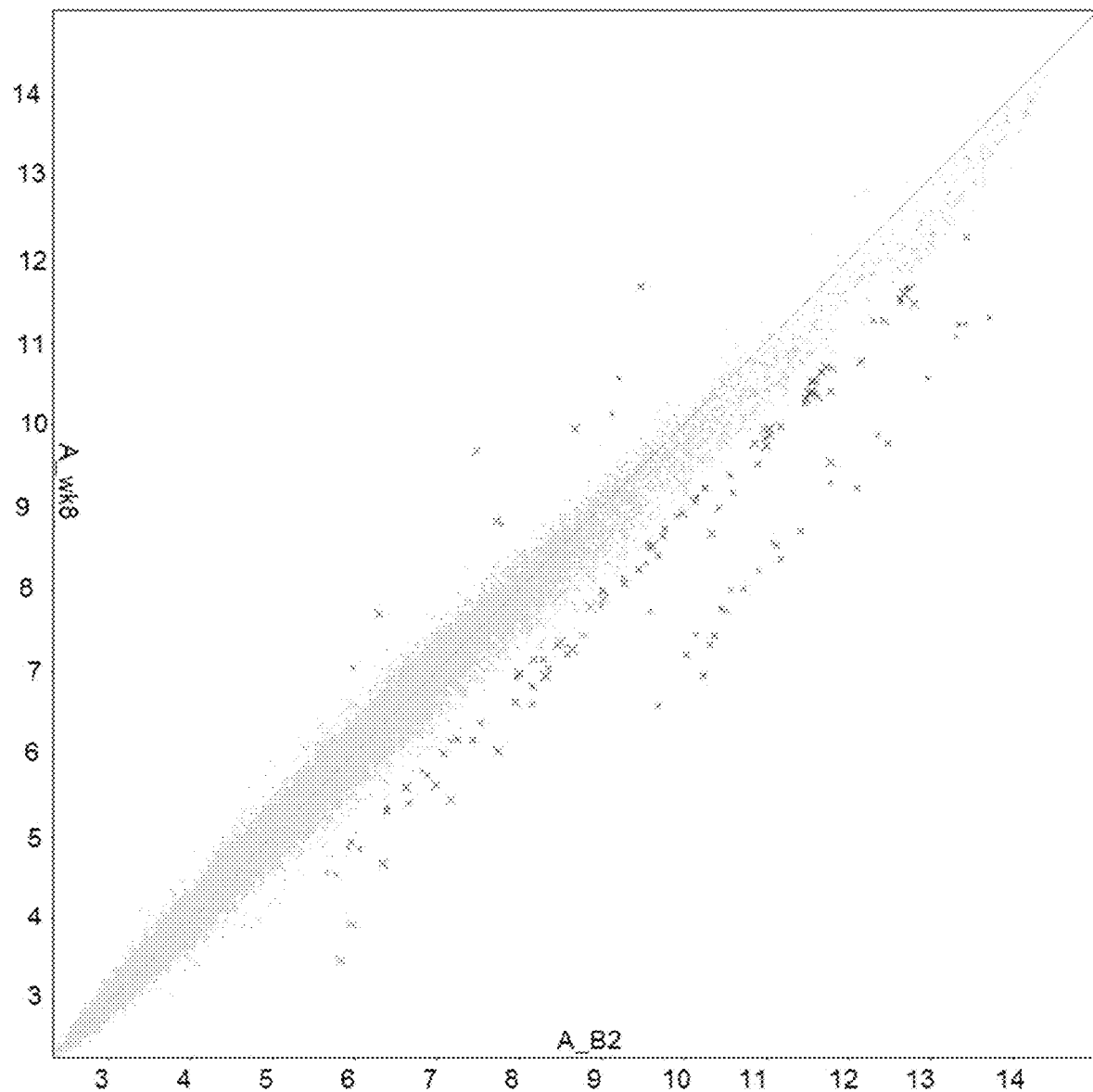
FIGS. 5A-5C graphically depict a ±2-fold change in gene expression in group A (FIG. 5A—test), group B (FIG. 5B—placebo), and group C (FIG. 5C—control) at baseline (x-axis) verses week 8 (y-axis) following exposure to group treatment. Outliers above the median represent probe sets upregulated by greater than 2-fold. Outliers below the median represent probes sets downregulated by greater than 2-fold.
Figure 5B:
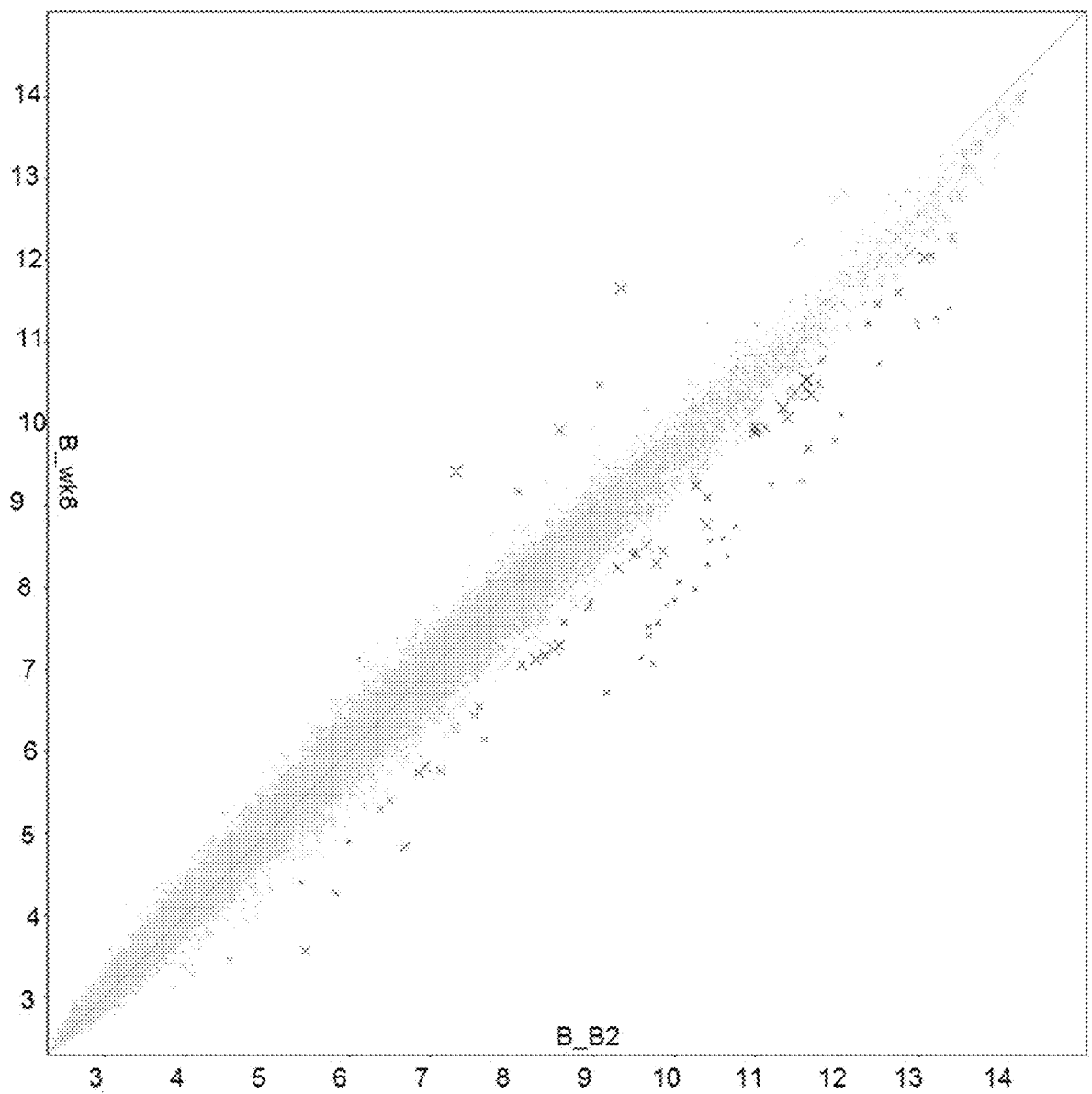
Figure 5C:
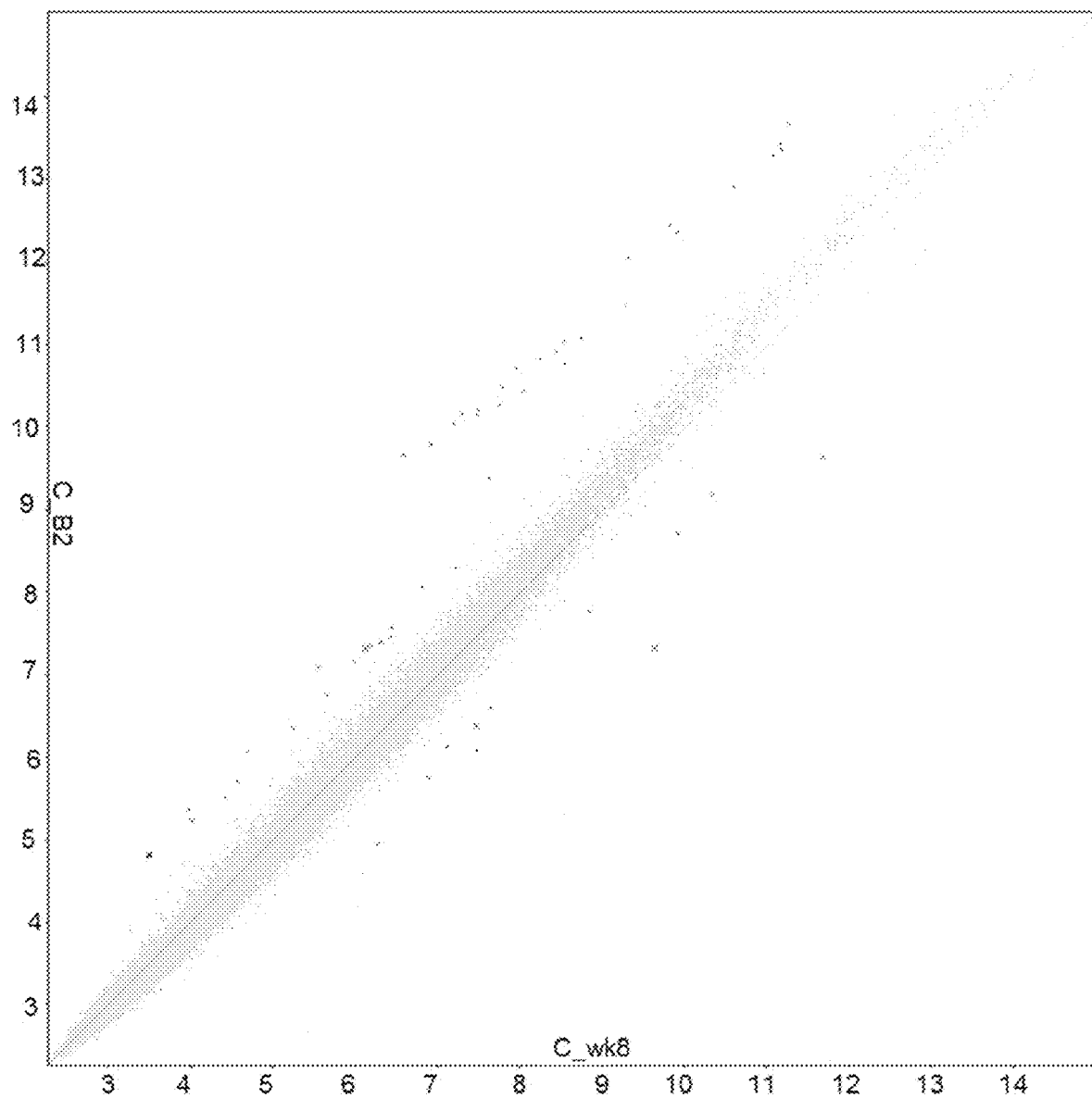

A total of 49372 probes were available for evaluation. The analysis was performed as shown in FIG. 4. Scatterplots evaluating differential expression between the baseline sample and the 8-week sample were generated for each group (FIGS. 5A-5C). Significantly more probe sets were up regulated and down regulated at the threshold levels in all groups as compared to the baseline versus 1-week differential expression data.

Group A b2 vs. wk8 samples were evaluated for 2-fold changes in expression. 53 probes representing 49 genes showed differential expression at significant levels (>2-fold changes with Bonferroni corrected p-values of $<1.0\times10^{-6}$).

After identifying the probes showing differential expression, other probes in the same 49 genes were evaluated for similar trends in expression. 37 genes showed differentially expressed data trends across multiple probe sets.

The 37 genes showing differentially expressed data trends were evaluated in the group B week 8 data (b2 vs. wk8). Genes showing differential expression in this placebo group were eliminated as candidates for differential expression related to the consumption of the product. 17 genes remained that were differentially expressed at significant levels in only the Group A, b2 vs. wk 8, set. After identification of these 17 genes all other probes on the microarray in each of those genes were examined for differential expression (Table 2). The 17 genes/probes most likely to have differential expression were all trending to be down regulated.

The 17 genes were identified as differentially expressed at greater than a 2-fold change with significant corrected p-values that were not differentially expressed in the placebo or control groups at the significance threshold.

TABLE 2

Genes with Differential Expression (Group A baseline vs. wk 8)

| Gene Symbol | Fold Change | ANOVA p-value | FDR p-value | Transcript Cluster ID |
|---|---|---|---|---|
| BLOC1S1 | −2.19 | 7.22E−09 | 0.000018 | 11716289_a_at |
| CALM2 | −1.02 | 0.465441 | 0.647335 | 11725960_s_at |
| CALM2 | −1.04 | 0.357166 | 0.551459 | 11725958_s_at |
| CALM2 | −1.05 | 0.062477 | 0.183958 | 11763258_x_at |
| CALM2 | −1.12 | 0.004751 | 0.035136 | 11725959_x_at |
| CALM2 | −1.21 | 0.014504 | 0.072744 | 11744198_s_at |
| CALM2 | −1.49 | 2.09E−08 | 0.000027 | 11753706_a_at |
| CALM2 | −2.11 | 2.11E−08 | 0.000027 | 11754149_s_at |
| CASP4 | 1.39 | 0.049944 | 0.159156 | 11760221_at |
| CASP4 | 1.17 | 0.078754 | 0.213334 | 11760491_at |
| CASP4 | −1.07 | 0.554356 | 0.718383 | 11760222_x_at |
| CASP4 | −1.35 | 0.000302 | 0.006149 | 11746002_a_at |
| CASP4 | −2.04 | 0.000005 | 0.000513 | 11716760_x_at |
| CASP4 | −2.04 | 0.000007 | 0.000665 | 11748529_x_at |
| CASP4 | −2.51 | 0.000000168 | 0.000079 | 11716759_a_at |
| CCDC107 | −1.19 | 0.110579 | 0.264735 | 11751801_a_at |
| CCDC107 | −1.26 | 0.002617 | 0.024088 | 11755734_x_at |
| CCDC107 | −1.38 | 0.000429 | 0.007626 | 11732672_x_at |
| CCDC107 | −1.42 | 0.000339 | 0.006578 | 11732670_a_at |
| CCDC107 | −2.07 | 7.05E−08 | 0.000051 | 11732671_s_at |
| CD63 | −1.62 | 0.000004 | 0.000478 | 11757417_x_at |
| CD63 | −1.95 | 7.16E−09 | 0.000018 | 11744260_a_at |
| CORO1B | −1.13 | 0.003558 | 0.029165 | 11758178_s_at |
| CORO1B | −1.18 | 0.0004 | 0.007283 | 11761218_x_at |
| CORO1B | −1.21 | 0.024903 | 0.10216 | 11761217_at |
| CORO1B | −1.3 | 0.000038 | 0.001726 | 11717487_x_at |
| CORO1B | −2.07 | 0.000000381 | 0.000131 | 11718849_at |
| FKBP3 | −2.01 | 0.000000109 | 0.000066 | 11719478_a_at |
| HM13 | 1.05 | 0.606639 | 0.757832 | 11736301_at |
| HM13 | −1.24 | 0.000032 | 0.001554 | 11740470_x_at |
| HM13 | −1.25 | 0.000262 | 0.005639 | 11716647_x_at |
| HM13 | −1.47 | 0.000000206 | 0.000089 | 11723017_x_at |
| HM13 | −1.71 | 0.000005 | 0.000534 | 11716646_a_at |
| HM13 | −1.97 | 0.00000069 | 0.000195 | 11723016_a_at |
| NDFIP1 | 1.09 | 0.511513 | 0.685758 | 11715512_s_at |
| NDFIP1 | −1.08 | 0.10596 | 0.257655 | 11715513_s_at |
| NDFIP1 | −1.49 | 0.000000664 | 0.000188 | 11715511_x_at |
| NDFIP1 | −1.62 | 0.000000162 | 0.000078 | 11715510_s_at |
| NDFIP1 | −2.01 | 2.17E−08 | 0.000027 | 11715509_a_at |
| NDUFB7 | −1.96 | 0.000000825 | 0.000207 | 11718991_a_at |
| NFKBIA | −1.29 | 0.001062 | 0.013486 | 11745878_x_at |
| NFKBIA | −2.06 | 0.000002 | 0.000337 | 11744000_a_at |
| NFKBIA | −2.09 | 0.000000457 | 0.000145 | 11757894_x_at |
| PRELID1 | −2.11 | 5.06E−08 | 0.000042 | 11725315_x_at |
| RPL27 | −1.66 | 0.000013 | 0.000937 | 200025_PM_s_at |
| RPL27 | −1.81 | 0.000013 | 0.000951 | 11757328_x_at |
| RPL27 | −2.19 | 0.000000409 | 0.000137 | 11718051_a_at |
| RPL30 | −1.21 | 0.002765 | 0.024852 | 200062_PM_s_at |
| RPL30 | −1.4 | 0.000707 | 0.010383 | 11757356_x_at |
| RPL30 | −1.58 | 0.000042 | 0.001815 | 11753659_x_at |
| RPL30 | −2.16 | 0.000000719 | 0.000196 | 11720954_s_at |
| SSR2 | −1.36 | 0.000006 | 0.000576 | 11715457_x_at |
| SSR2 | −2.67 | 0.00000091 | 0.000219 | 11715456_a_at |
| UBL5 | −1.94 | 3.13E−08 | 0.000034 | 11715756_x_at |
| UBL5 | −2.1 | 2.85E−08 | 0.000034 | 11757646_x_at |
| UQCR11 | −1.14 | 0.013123 | 0.068337 | 11716307_at |
| UQCR11 | −2.01 | 0.000000149 | 0.000076 | 11757334_a_at |

Figure 6:
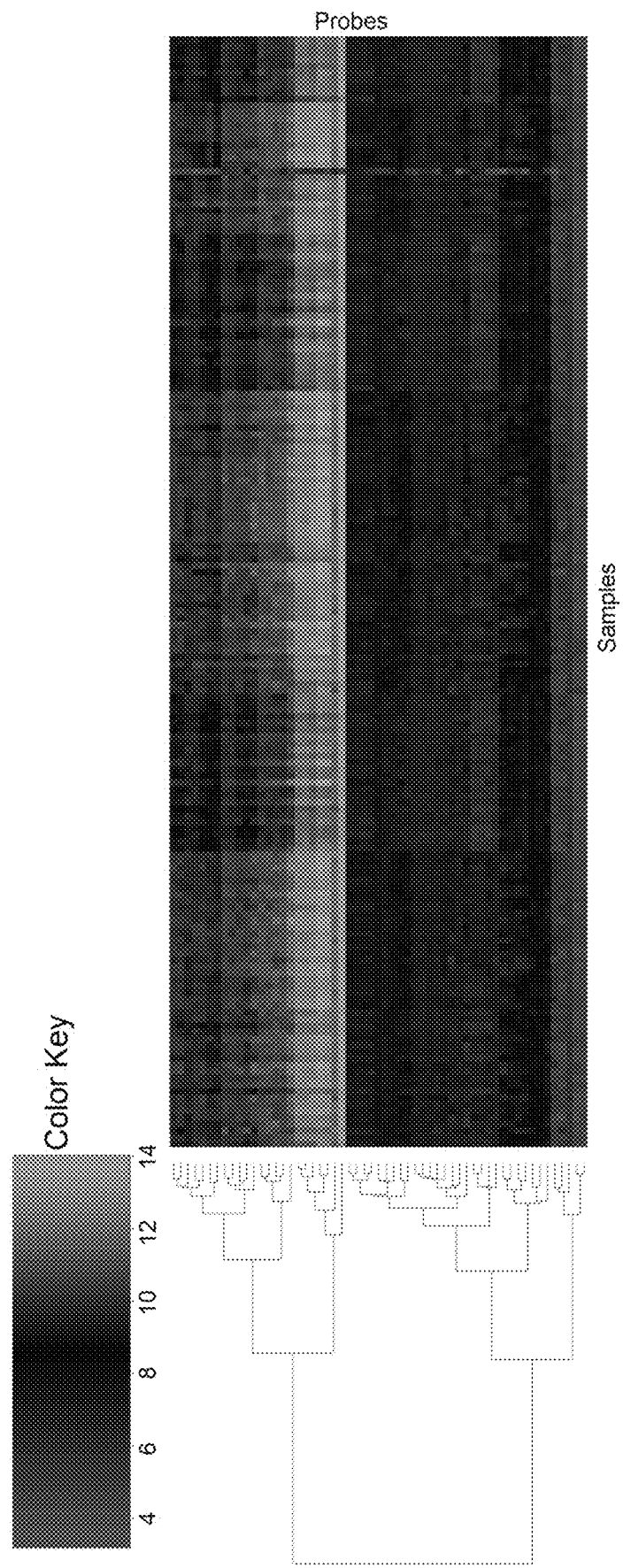
FIG. 6 illustrates a heat map of 57 probes with significant differential expression across all samples in group A compared to the baseline or week 1 experiment at study thresholds.

As shown in the heat map (FIG. 6), 17 genes show differential expression in group A at week 8 compared to the baseline or week 1 experiment at the study thresholds. Heat map comparison of the 3 groups showed similar trends across all baseline versus week 8 comparisons implying the same trending of differential expression in the placebo and control groups, B and C respectively. These results were significant due to the fact that the Group A results were above the study threshold.

Based on these results, further analysis was performed using unpaired ANOVA analysis between group A (wk8) versus group B (wk8). No differential expression changes were observed in genes at 2-fold change level.

Because there appeared to be little to no change in the expression data when held to a 2× fold change and corrected p-value threshold and not occurring in the other groups, we looked to find genes that had an nominal p-value of $p<0.05$ that demonstrated consistent change compared with the placebo group. ANOVA unpaired analysis of group A_wk8 vs group B_wk8 with a nominal p-value of $<0.05$ was completed to identify potentially differentially expressed genes. Each group had 24 samples available for analysis. This analysis revealed 11 probes sets (11 genes) that met these criteria (Table 3). All probes in those genes were then examined for trends.

TABLE 3

Genes with Differential Expression (Group A wk 8 vs. Group B wk 8)

| Gene Symbol | Fold Change (linear) (A_WK8 vs. B_WK8) | ANOVA p-value (A_WK8 vs. B_WK8) | Transcript Cluster ID |
|---|---|---|---|
| KCTD12 | -1.06 | 0.323863 | 11715947_a_at |
| KCTD12 | -1.21 | 0.103912 | 11715948_at |
| KCTD12 | -1.21 | 0.039723 | 11715949_s_at |
| KCTD12 | -1.06 | 0.315231 | 11715950_a_at |
| KCTD12 | -1.08 | 0.311953 | 11715951_s_at |
| DNAJC3 | -1.05 | 0.508502 | 11717372_s_at |
| DNAJC3 | -1.2 | 0.013674 | 11717373_at |
| DNAJC3 | -1.08 | 0.180221 | 11717374_at |
| EGR1 | 1.22 | 0.00051 | 11717860_a_at |
| EGR1 | 1.04 | 0.184945 | 11717861_a_at |
| EGR1 | -1.05 | 0.540634 | 11717862_x_at |
| EMB | -1.25 | 0.049527 | 11722887_x_at |
| PYROXD1 | -1.31 | 0.044862 | 11723800_x_at |
| PYROXD1 | -1.11 | 0.267704 | 11723801_s_at |
| WDR11 | -1.2 | 0.026049 | 11726517_s_at |
| IRAK3 | -1.2 | 0.054293 | 11726894_a_at |
| IRAK3 | -1.2 | 0.016879 | 11726895_a_at |
| IRAK3 | -1.28 | 0.020403 | 11726896_a_at |
| CCR10 | 1.2 | 0.003348 | 11729900_at |
| CCDC126 | -1.05 | 0.14749 | 11730359_a_at |
| CCDC126 | -1.22 | 0.008698 | 11730360_at |
| CCDC126 | -1 | 0.590658 | 11730361_at |
| IRAK3 | -1.09 | 0.419533 | 11742017_a_at |
| PYROXD1 | -1.05 | 0.077593 | 11747953_s_at |
| PYROXD1 | 1.02 | 0.747469 | 11747954_x_at |
| WDR11 | -1.04 | 0.434389 | 11750116_a_at |
| EGR1 | 1.07 | 0.358741 | 11751643_x_at |
| EGR1 | 1 | 0.583142 | 11752940_a_at |
| EGR1 | 1.02 | 0.852381 | 11754334_s_at |
| IGLV1-41; IGLV1-51 | 1.29 | 0.03319 | 11763225_x_at |
| IGLV1-41 | 1.19 | 0.015031 | 11763237_x_at |

Figure 7:
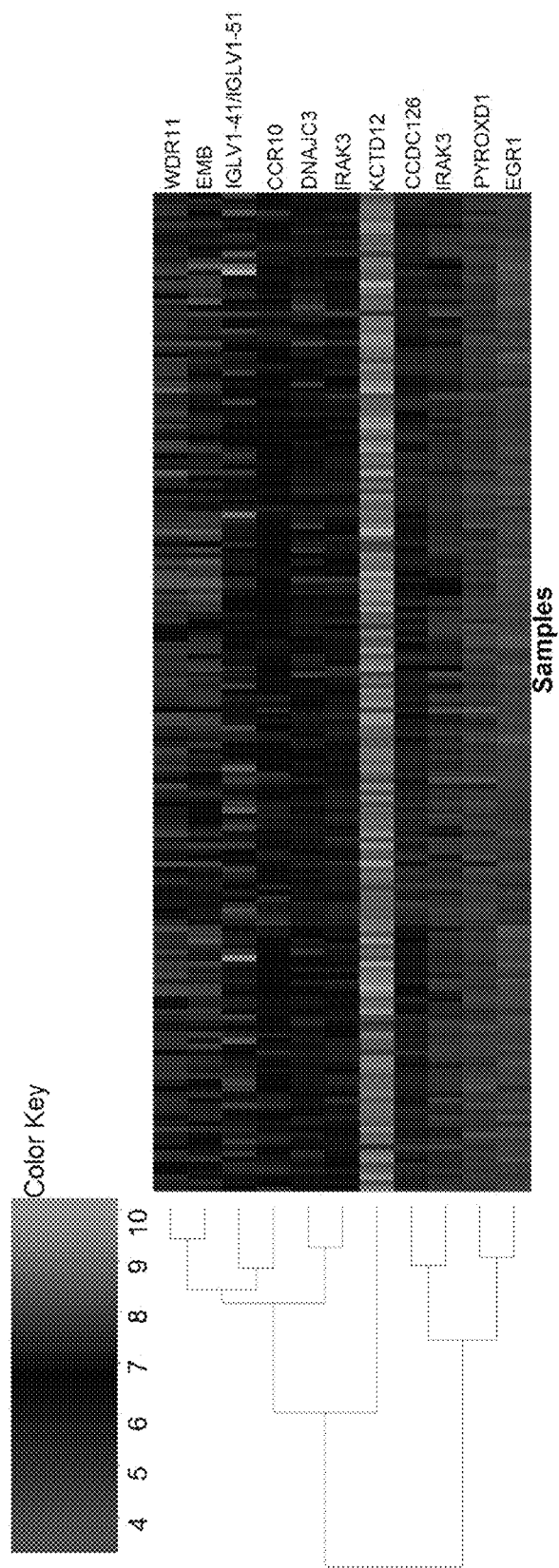
FIG. 7 illustrates a heat map of 11 genes that had a nominal p-value of p<0.05 that demonstrated consistent change compared with the placebo group. The eleven probes showed significant differential expression across all samples in group A compared to the baseline or week 1 experiment at study thresholds.

For the 11 probes identified as differentially expressed, the fold change was considered in the Group A b2 vs. wk 8 and in Group B b2 vs. wk 8 to identify that the difference observed was due to changes in the test group (Table 4). These values yielded fold changes of +/−0.2-0.3, representing a 20-30% change in transcription. The heat map across all samples supported this data (FIG. 7).

TABLE 4

Probes with Differential Expression (Group A wk 8 vs Group B wk 8 compared to baseline vs. wk 8 in groups A and B)

| Gene Symbol | Transcript Cluster ID | Fold Change (linear) (A_WK8 vs. B_WK8) | Fold Change (linear) (A_WK8 vs. A_B2) | Fold Change (linear) (B_WK8 vs. B_B2) |
|---|---|---|---|---|
| KCTD12 | 11715949_s_at | -1.21 | -1.17 | 1.1 |
| DNAJC3 | 11717373_at | -1.2 | -1.21 | -1.11 |
| EGR1 | 11717860_a_at | 1.22 | 1.4 | 1 |
| EMB | 11722887_x_at | -1.25 | -1.21 | -1.15 |
| PYROXD1 | 11723800_x_at | -1.31 | -1.25 | 1.03 |
| WDR11 | 11726517_s_at | -1.2 | -1.11 | -1.1 |
| IRAK3 | 11726895_a_at | -1.2 | -1.26 | -1.06 |
| IRAK3 | 11726896_a_at | -1.28 | -1.14 | 1.01 |
| CCR10 | 11729900_at | 1.2 | 1.19 | 1.02 |
| CCDC126 | 11730360_at | -1.22 | -1.32 | -1.09 |
| IGLV1-41; IGLV1-51 | 11763225_x_at | 1.29 | 1.34 | 1.22 |

Five probes showed a fold change from baseline to week 8 in the B group that was less than +1.05 (5%), suggesting that the 20-31% fold change observed in the group A wk 8 vs. group B wk 8 was due to differences in the change from baseline and week 8 in group A rather than group B. An additional probe in the IRAK3 gene was near this threshold. These gene/probe combinations were not differentially expressed in group C.

Figure 8:
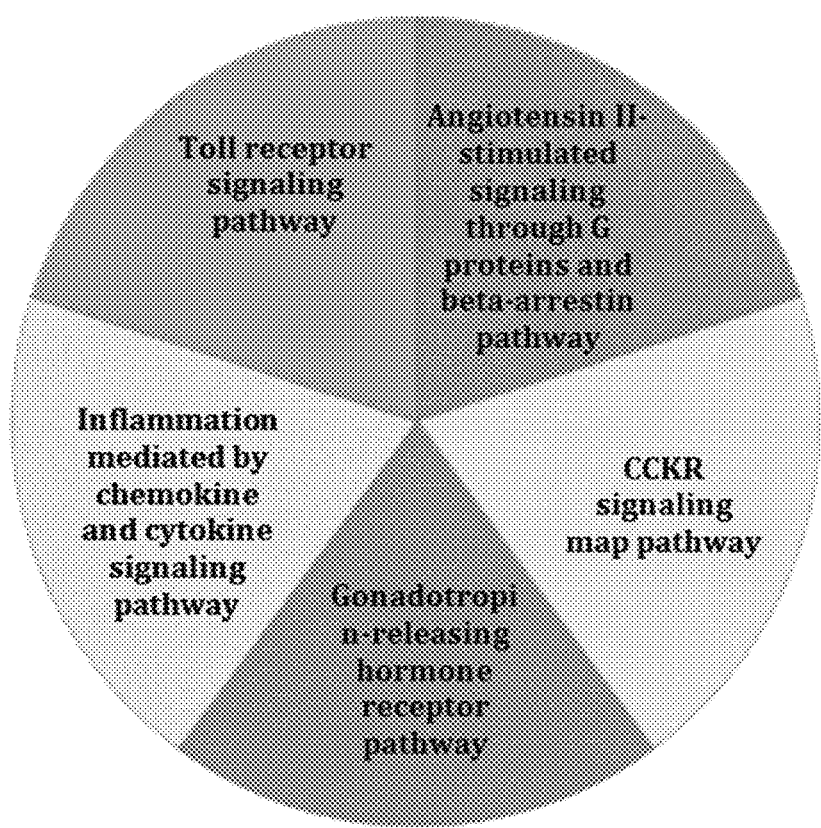
FIG. 8 illustrates a protein analysis through evolutionary relationship (PANTHER) diagram of the eleven genes of FIG. 7, which show five pathway hits involving 3 genes, CCR10, EGR1, and IRAK3.

PANTHER (Protein ANalysis THrough Evolutionary Relationships) is a classification system designed to classify proteins (and their genes) in order to understand gene pathways using high-throughput analysis. Using Panther Pathway Analysis (v11.1) the 11 genes of interest had 5 pathway hits (Table 5 and FIG. 8). The 5 pathway hits involved 3 genes, CCR10, EGR1 and IRAK3, all which were genes that showed differential expression most likely due to changes from baseline to week 8 in group A.

TABLE 5

Panther Pathway Analysis

| Gene | Pathway 1 | Pathway 2 | Pathway 3 |
|---|---|---|---|
| CCDC126 | none | | |
| CCR10 | Inflammation mediated by chemokine and cytokine signaling pathway | | |
| DNAJC3 | none | | |
| EGR1 | Angiotensin II–stimulated signaling through G proteins and beta-arrestin | CCKR signaling map | Gonadotropin-releasing hormone receptor pathway |
| EMB | none | | |
| IGLV1-41 | none | | |
| IGLV1-51 | none | | |
| IRAK3 | Toll receptor signaling pathway | | |
| KCTD12 | none | | |
| PYROXD1 | none | | |
| WDR11 | none | | |

Another pathway analysis software, Wikipathways, was also used to look for pathways associated with the genes of interest. Analysis revealed similar pathways for the genes identified in the Panther analysis along with pathways for DNAJC3 and EMB genes (Table 6).

TABLE 6

WikiPathways Analysis

| Gene | Pathway 1 | Pathway 2 | Pathway 3 | Pathway 4 | Pathway 5 |
|---|---|---|---|---|---|
| CCDC126 | None | | | | |
| CCR10 | Peptide GPCRs | GPCRs, Class A Rhodopsin-like | Chemokine signaling pathway | GPCR ligand binding | GPCR downstream signaling |
| DNAJC3 | Photodynamic therapy-induced unfolded protein response | XBP1 (S) activates chaperone genes | Influenza Life Cycle | | |
| EGR1 | Serotonin Receptor 4/6/7 and NR3C Signaling | Brain-Derived Neurotrophic Factor (BDNF) signaling pathway | Circadian rhythm related genes | NRF2 pathway | VEGFA-VEGFR2 Signaling Pathway |
| EMB | Transport of glucose and other sugars, bile salts and organic | | | | |

TABLE 6-continued

WikiPathways Analysis

| Gene | Pathway 1 | Pathway 2 | Pathway 3 | Pathway 4 | Pathway 5 |
| --- | --- | --- | --- | --- | --- |
| | acids, metal ions and amine compounds | | | | |
| IGLV1-41 | None | | | | |
| IGLV1-51 | None | | | | |
| IRAK3 | Interleukin-1 signaling pathway | Regulation of toll-like receptor signaling pathway | MyD88:Mal cascade initiated on plasma membrane | | |
| KCTD12 | None | | | | |
| PYROXD1 | None | | | | |
| WDR11 | None | | | | |

The primary analysis did not reveal any significant ±2-fold changes with significant p-values. Additional analysis identified at least 5 genes that may have interesting differential expression in the test group and were not significant in placebo or control groups, when comparing the baseline expression to the week-8 expression.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of modulating expression of a gene in a cell comprising contacting the cell with a composition comprising an electrolyzed saline solution, the electrolyzed saline solution comprising a mixture of reduced species and reactive species, thereby modulating expression of the gene, wherein the electrolyzed saline solution comprises $HOCl^{-1}$, $OCl^{-1}$, $Cl^{-1}$, $Cl_2$, $O_2^3$, $O_3$, and $H_2O_2$.

2. The method of claim 1, wherein the cell is an isolated cell.

3. The method of claim 1, wherein the modulating expression of the gene comprises changing expression of the gene, and wherein the method further comprises detecting the change in expression of the gene.

4. The method of claim 3, wherein the cell is located in situ in a subject, and wherein detecting comprises inferring a change in the expression of the gene from a physiological change in the subject.

5. The method of claim 3, wherein detecting comprises performing one or more of ELISA, immunohistochemistry, Northern blot, Southern blot, or PCR.

6. The method of claim 1, wherein the cell is located in situ in a subject, and wherein contacting comprises administering to the subject an amount of the composition effective to modulate expression of the gene.

7. The method of claim 6, wherein the subject is human.

8. The method of claim 6, wherein the composition is administered orally.

9. The method of claim 6, wherein the composition is administered in an amount of about 0.1 ounce to about 12 ounces at a frequency of four times daily to one time monthly for a period of one day to 10 years.

10. The method of claim 1, wherein the gene encodes C-C chemokine receptor type 10 (CCR10), coiled-coil domain-containing protein 126 (CCDC126), DnaJ homolog subfamily C member 3 (DNAJC3), early growth response protein 1 (EGR1), embigin (EMB), immunoglobulin lambda variable 1-41 (IGLV1-41), immunoglobulin lambda variable 1-51 (IGLV1-51), interleukin-1 receptor-associated kinase 3 (IRAK3), potassium channel tetramerization domain containing 12 (KCTD12), pyridine nucleotide-disulfide oxidoreductase domain 1 (PYROXD1), or WD repeat-containing protein 11 (WDR11).

11. The method of claim 1, wherein the composition has a pH between about 6 and about 9.

12. The method of claim 1, wherein the composition comprises a solution containing 1000 ppm to 1400 ppm sodium, 1200 ppm to 1600 ppm chloride, 16 ppm to 24 ppm hypochlorous acid, at least 94 µM superoxide radical, and at least 241 µM hydroxyl radical.

13. The method of claim 1, wherein the one or more reactive species comprises one or more of active chlorine species in an amount of about 5 to about 300 ppm, active oxygen species in an amount of about 0.1 to about 300 ppm, or active hydrogen species in an amount of about 5 to about 300 ppm.

14. The method of claim 13, wherein the active chlorine species comprises at least one of an active chlorine species selected from the group consisting of: free chlorine, hypochlorous acid and hypochlorite ion.

15. The method of claim 14, wherein the electrolyzed saline solution is prepared using a saline solution with a starting sodium chloride solution selected from the group consisting of: 0.9% NaCl (w/vol), 0.45% NaCl (w/vol), and 0.215% NaCl (wt/vol).

16. The method of claim 1, wherein the electrolyzed saline solution is prepared by subjecting a saline solution comprising sodium chloride in an amount of about 0.05 to about 10% to electrolysis under conditions sufficient to produce the one or more reactive species.

17. The method of claim 1, wherein expression of the gene is modulated by greater than 2 fold change compared to expression of the gene in an untreated cell.

18. The method of claim 1, wherein gene expression is increased in CCDC126, CCR10, EGR1, IGLV1-41, or IGLV1-51.

19. The method of claim 1, wherein gene expression is decreased in DNAJC3, EMB, IRAK3, KCTD12, PYROXD1, or WDR11.

20. A method of modulating expression of a gene in a cell comprising contacting the cell with a composition comprising an electrolyzed saline solution, the electrolyzed saline solution comprising a mixture of reduced species and reactive species, thereby modulating expression of the gene, wherein the composition comprises a solution containing 1000 ppm to 1400 ppm sodium, 1200 ppm to 1600 ppm chloride, 16 ppm to 24 ppm hypochlorous acid, at least 94 µM superoxide radical, and at least 241 µM hydroxyl radical.

21. The method of claim 20, wherein the modulating expression of the gene comprises changing expression of the gene, and wherein the method further comprises detecting the change in expression of the gene.

22. The method of claim 20, wherein the cell is located in situ in a subject, and wherein contacting comprises administering to the subject an amount of the composition effective to modulate expression of the gene.

23. The method of claim 20, wherein the gene encodes C-C chemokine receptor type 10 (CCR10), coiled-coil domain-containing protein 126 (CCDC126), DnaJ homolog subfamily C member 3 (DNAJC3), early growth response protein 1 (EGR1), embigin (EMB), immunoglobulin lambda variable 1-41 (IGLV1-41), immunoglobulin lambda variable 1-51 (IGLV1-51), interleukin-1 receptor-associated kinase 3 (IRAK3), potassium channel tetramerization domain containing 12 (KCTD12), pyridine nucleotide-disulfide oxidoreductase domain 1 (PYROXD1), or WD repeat-containing protein 11 (WDR11).

24. The method of claim 20, wherein the electrolyzed saline solution is prepared by subjecting a saline solution comprising sodium chloride in an amount of about 0.05 to about 10% to electrolysis under conditions sufficient to produce the one or more reactive species.

* * * * *